(12) United States Patent
Peskin

(10) Patent No.: US 8,431,165 B2
(45) Date of Patent: Apr. 30, 2013

(54) MEDICAMENT FOR TREATMENT OF CANCER AND OTHER DISEASES

(75) Inventor: Brian Peskin, Houston, TX (US)

(73) Assignee: Swing Aerobics Licensing, Inc., Houston, TX (US)

( * ) Notice: Subject to any disclaimer, the term of this patent is extended or adjusted under 35 U.S.C. 154(b) by 67 days.

(21) Appl. No.: 12/818,723

(22) Filed: Jun. 18, 2010

(65) Prior Publication Data

US 2010/0255126 A1 Oct. 7, 2010

Related U.S. Application Data

(63) Continuation-in-part of application No. 11/010,792, filed on Dec. 13, 2004, now Pat. No. 8,092,839.

(51) Int. Cl.
*A61K 36/00* (2006.01)
*A61K 36/63* (2006.01)
*A61K 36/30* (2006.01)
*A61K 36/889* (2006.01)
*A61K 36/736* (2006.01)
*A61K 36/55* (2006.01)

(52) U.S. Cl.
USPC .................... 424/725; 424/768; 424/758

(58) Field of Classification Search ........................ None
See application file for complete search history.

(56) References Cited

U.S. PATENT DOCUMENTS

| | | | |
|---|---|---|---|
| 4,309,415 A | 1/1982 | Horrobin | |
| 4,670,285 A | 6/1987 | Clandinin et al. | |
| 4,681,896 A | 7/1987 | Horrobin | |
| 4,931,468 A | 6/1990 | Horrobin | |
| 5,013,569 A | 5/1991 | Rubin | |
| 5,158,975 A | 10/1992 | Guichardant et al. | |
| 5,223,285 A * | 6/1993 | DeMichele et al. | 426/72 |
| 5,246,726 A | 9/1993 | Horrobin et al. | |
| 5,446,841 A | 8/1995 | Kitano et al. | |
| 5,457,130 A | 10/1995 | Tisdale et al. | |
| 5,466,841 A | 11/1995 | Horrobin et al. | |
| 5,562,913 A | 10/1996 | Horrobin | |
| 5,591,446 A | 1/1997 | Melnik et al. | |
| 5,599,840 A | 2/1997 | Yehuda | |
| 5,656,319 A | 8/1997 | Barclay | |
| 5,763,484 A | 6/1998 | Horrobin | |
| 5,766,571 A | 6/1998 | Ceriani et al. | |
| 5,776,913 A | 7/1998 | Ogilvie et al. | |
| 5,886,037 A | 3/1999 | Klor et al. | |
| 5,928,696 A | 7/1999 | Best et al. | |
| 6,005,004 A | 12/1999 | Katz et al. | |
| 6,083,536 A | 7/2000 | Macrides et al. | |
| 6,159,506 A | 12/2000 | Bieser et al. | |
| 6,159,507 A | 12/2000 | Igarashi | |
| 6,340,705 B1 | 1/2002 | Obukowicz et al. | |
| 6,471,969 B1 | 10/2002 | Schlachter et al. | |
| 6,479,544 B1 | 11/2002 | Horrobin | |
| 6,607,755 B2 | 8/2003 | Farley | |
| 6,656,969 B2 | 12/2003 | Young | |
| 6,726,941 B2 | 4/2004 | Ethington, Jr. et al. | |
| 2002/0001599 A1 * | 1/2002 | Neubourg | 424/400 |
| 2002/0010211 A1 | 1/2002 | Obukowicz et al. | |
| 2002/0146463 A1 | 10/2002 | Clayton | |
| 2003/0000391 A1 * | 1/2003 | Highman et al. | 99/275 |
| 2003/0163845 A1 | 8/2003 | Mukerji et al. | |
| 2004/0058024 A1 * | 3/2004 | Surette | 424/773 |
| 2004/0170583 A1 * | 9/2004 | Heeg et al. | 424/59 |
| 2004/0213864 A1 | 10/2004 | Slimak | |
| 2004/0234579 A1 | 11/2004 | Finke | |
| 2005/0100584 A1 | 5/2005 | Miller et al. | |
| 2006/0068019 A1 | 3/2006 | Dalziel et al. | |

FOREIGN PATENT DOCUMENTS

| | | | |
|---|---|---|---|
| CN | 1270160 A | * | 10/2000 |
| CN | 1292411 A | * | 4/2001 |
| CN | 1312071 A | * | 9/2001 |
| DE | 29918993 U1 | * | 3/2001 |
| GB | 2341317 A | * | 3/2000 |
| GB | 2378693 A | | 2/2003 |
| HU | 9600336 A2 | * | 12/1997 |
| JP | 2001/218558 A | | 8/2001 |
| WO | WO 97/13415 | | 4/1997 |
| WO | WO 98/09621 A1 | | 3/1998 |
| WO | WO 98/16215 | | 4/1998 |

OTHER PUBLICATIONS

Picuric-Jovanovic et al, Compositional components and the oxidative stability of *Ribes nigrum* seed oil, Journal of Herbs, Spices & Medicinal Plants (2002), 10(1), 37-43.*
Castillo et al, Genotypic variation in fatty acid content of blackcurrant seeds, J. Agric. Food. Chem. 2002, 50: 332-335.*
Barre et al, The effect of borage oil consumption on human plasma lipid levels and the phosphatidylcholine and cholesterol ester composition of high density lipoprotein. Nutrition Research, 1992, 12 (10): 1181-1194.*
Rahma et al, Chemical Characterization of Peach kernel oil and protein: functional properties, in vitro digestibility and amino acids profile of the flour, Food Chemistry 28 (1988) 31-43.*
Guo et al, Properties and use of the seed oil of *Malia azedarach* L, Tianran Chanwu Yanjui Yu Kaifa (1995), 7(1), 82-7.*
Huang et al. Preparation of *Camelina sativa* seed oil by cold-pressing and its refining technology, Zhonghuo Youzhi (2006), 31 (1), 17-20.*
Andersson et al., "Fatty Acid Profile of Skeletal Muscle Phospholipids in Trained and Untrained Young Men," Am. J. Physiol. Endocrinol. Metab., 2000, pp. E744-E751, vol. 279.

(Continued)

*Primary Examiner* — Qiuwen Mi
(74) *Attorney, Agent, or Firm* — Foley & Lardner LLP

(57) ABSTRACT

A medicament for the treatment of cancer and other diseases, including cardiovascular diseases, by increasing cellular oxygenation is described wherein a composition of organically grown, chemically unprocessed and unrefined oils is used that provides a ratio of parent omega-6 to parent omega-3 that is greater than 1:1 and preferably within a range from about 1.1:1 to about 5:1. Most preferably, the ratio is about 2.6:1. The medicament may be administered via capsule or liquid form and preferably on a periodic basis, such as daily. In further embodiments, the medicament may be applied in topical ointment form.

18 Claims, 1 Drawing Sheet

OTHER PUBLICATIONS

Baumann & Rusch, "Effect of Diet on Tumors Induced by Ultraviolet Light," American Journal of Cancer, 1939, pp. 213-221, vol. 35.

Begin et al., "Differential Killing of Human Carcinoma Cells Supplemented with n-3 and n-6 Polyunsaturated Fatty Acids," JNCI, 1986, pp. 1053-1062, vol. 77, No. 5.

Biryukova et al., Study of biological value of liquid mix/vegetable mixture for infant feeding, Tekhnologiya novykh produktov dlya detskogo I lechebnogo pitaniya, 1983, pp. 52-57, vol. 80.

Booyens et al., "Dietary Fats and Cancer," Medical Hypotheses, 1985, pp. 351-362, vol. 17.

Buchanan et al., "Eicosanoids, Other Fatty Acid Metabolites and the Cardiovascular System: Are the Present Approaches Rational?" Prostaglandins in the Cardiovascular System, 1992, pp. 273-281.

Burns et al., "Effect of Modification of Plasma Membrane Fatty Acid Composition on Fluidity and Methotrexate Tranport in L1210 Murine Leukemia Cells," Cancer Research, 1979, pp. 1726-1732, vol. 39.

Burr et al., "A New Deficiency Disease Produced by the Rigid Exclusion of Fat from the Diet," Journal of Biological Chemistry, 1929, pp. 345-367, vol. LXXXII.

Calder, P.C., "ω3 Polyunsaturated Fatty Acids, Inflamation and Immunity," World Review of Nutrition and Dietetics: Fatty Acids and Lipids—New Findings, 2000, pp. 109-116, vol. 88.

Crawford, M.A., "Commentary on the Workshop Statement," Prostaglandins, Leukotrienes and Essential Fatty Acids, 2000, pp. 131-134, vol. 63, No. 3.

Das, U.N., "Essential Fatty Acids as Possible Mediators of the Actions of Statins," Prostaglandins, Leukotrienes and Essential Fatty Acids, 2001, pp. 37-40, vol. 65, No. 1.

Epstein, S., "The Stop Cancer Before It Starts Campaign: How to Win the Losing War Against Cancer," 2003, pp. 1-7.

Erdmann, R., "Fats That Can Save Your Life," 1990, pp. 88-89.

Eynard et al., "Dietary Deficiency or Enrichment of Essential Fatty Acids Modulates Tumorigenesis in the Whole Body of Cobalt-60-Irradiated Mice," Prostaglandins, Leukotrienes and Essential Fatty Acids, 1997, pp. 239-244, vol. 56, No. 3.

Eynard et al., "Eicosatrienoic Acid (20:3 n-9) Inhibits the Expression of E-Cadherin and Desmoglein in Human Squamous Cell Carcinoma in Vitro," Prostaglandins, Leukotrienes and Essential Fatty Acids, 1998, pp. 371-377, vol. 59, No. 6.

Eynard, A., "Is the Risk of Urinary Tract Tumerogenesis Enhanced by a Marginal Chronic Essential Fatty Acid Deficiency (EFAD)," Nutrition, 1998, pp. 211-216, vol. 14, No. 2.

Fahmin et al., "Effect of pumpkin-seed oil on the level of free redical scavengers induced during adjuvant-arthritis in rats," Pharmacological Research, 1995, pp. 73-79, vol. 31, No. 1).

Gazso et al., "Influence of Omega-3 Fatty Acids on the Prostaglandin-Metabolism in Healthy Volunteers and Patients Suffering from PVD," Prostaglandins in the Cardiovascular System, 1992, pp. 151-156.

Goldblatt & Cameron, "Induced Malignancy in Cells from Rat Myocardium Subjected to Intermittent Anaerobiosis During Long Propagation in Vitro," The Journal of Experimental Medicine, 1952, pp. 525-564, vol. 97.

Green et al., "Low eruic acid canola oil does not induce heart triglyceride accumulation in Neonatal pigs fed formula," Lipids, 2000, vol. 35, No. 6.

Iacono et al., "The Role of Dietary Essential Fatty Acids and Prostaglandins in Reducing Blood Pressure," Progress in Lipids Research, 1981, pp. 349-364, vol. 20.

Jiang et al., "Gamma Linolenic Acid Regulates Expression of Maspin and the Motility of Cancer Cells," Biochemical and Biophysical Research Communications, 1997, pp. 639-644, vol. 237.

Klein et al., "Low Alpha-lineolic Acid Content of Adipose Breast Tissue is Associated with an Increased Risk of Breast Cancer," European Journal of Cancer, 2000, pp. 335-340, vol. 36.

Lands et al., "Quantitative Effects of Dietary Polyunsaturated Fats on the Composition of Fatty Acids in Rat Tissues," Lipids, 1990, pp. 505-516, vol. 25, No. 9.

Lehninger, A., Short Course in Biochemistry 1973, p. 109.

Lopes et al., "Reduced inflammatory response in rats fed fat-rich diets role of leukotrienes," Life Sciences, 2000, pp. 13-21, vol. 67, No. 1.

Makrides et al., "A randomized trial of different ratios of linoleic to a-linolenic acid in the diet of term infants: effects on visual function and growth," Am J Clin Nutr, 2000, pp. 120-129, vol. 71.

Meisenberg & Simmons, Principles of Medical Biochemistry, 1998, pp. 377-378, vol. 226.

Murray et al., Harper's Illustrated Biochemistry, 26'0 Edit., 2003, pp. 90, 93, 191, 193 and 418.

Prottey et al., "Correction of the Cutaneous Manifestations of Essential Fatty Acid Deficiency in Man by Application of Sunflower-Seed Oil to the Skin," The Journal of Investigative Dermatology, 1975, pp. 228-234, vol. 64.

Purasiri et al., "Effect of Essential Fatty Acids on Natural Cytotoxicity in Patients with Colorectal Cancer," European Journal of Surgical Oncology, 1995, pp. 254-260, vol. 21.

Rassias et al., "Linoleic Acid Lowers LDL Cholesterol without a Proportionate Displacement of Saturated Fatty Acid," European Journal of Clinical Nutrition, 1990, pp. 315-320, vol. 45.

Salem, Jr. et al., "Alpha-Linolenic Acid Conversion Revisited," PUFA Newsletter, 2003, p. 3.

Santos et al, "Fatty acids essential in nutrition," *Agronomia lusitana*, 1953, pp. 193-242, vol. 15.

Schmidt, M.A., Smart Fats: How Dietary Fats and Oils Affect Mental, Physical and Emotional Intelligence, 1997, pp. 27-29.

Sinclair et al., "What is the Role of a-Linolenic Acid for Mammals," Lipids, 2002, pp. 1113-1123, vol. 37, No. 12.

Sinclair, H.M., "Essential Fatty Acids in Perspective," Human Nutrition: Clinical Nutrition, 1984, pp. 245-260, vol. 38C.

Takahashi et al., "Effect of ω3 and ω6 Fatty Acids on Transformation of Cultured Cells by Irradiation and Transfection," Cancer Research, 1992, pp. 154-162, vol. 52.

Wainwright et al., "The Effects of Dietary n-3/n-6 Ratio on Brain Development in the Mouse: A Dose Response Study with Long-Chain n-3 Fatty Acids," Lipids, 1992, pp. 98-103, vol. 27, No. 2.

Warburg, O., "On the Origin of Cancer Cells," Science, 1956, pp. 309-314.

Warburg, O., "The Prime Cause and Prevention of Cancer—Part 1," Revised Lecture at the Meeting of the Nobel-Laureates on Jun. 30, 1966, pp. 1-9.

Warburg, O., "The Prime Cause and Prevention of Cancer—Part 2," Revised Lecture at the Meeting of the Nobel-Laureates on Jun. 30, 1966, pp. 1-5.

The Notice of References Cited (PTO-892) in the U.S. Appl. No. 11/010,792, dated Jul. 21, 2010.

Udo's choice oil blend-supplement review, www.t-mag.com, Oct. 31, 2003.

Bell, "Effects of a commercial soy lecithin preparation on development of sensorimotor behavior and brain biochemistry in the rat", Developmental Psychobiology, vol. 18, No. 1, 1995, pp. 59-66.

Collins, "Anti-malignancy factors apparently present in organically grown food", Advan Frotiers Plant Sci, vol. 1, 1962, pp. 31-33.

Edem, "Palm oil: Biochemical, physiological, nutritional, hematological, and toxicological aspects: a review", Plant food for human nutrition, vol. 57, 2002, pp. 319-341.

The Notice of References cited in U.S. Appl. No. 11/010,792, dated Jun. 13, 2003.

Leson et al., "Hemp seed and hemp oil, Cannabis and Cannabinoids: Pharmacology, Toxicology," Haworth Integrative Healing Press New York, 2002, pp. 411-425.

Leong et al., "Palm tocotrienol complex," Vitamin E of the 21$^{st}$ century, Agro-Food-Industry Hi-Tech, 2001, pp. 22-24, vol. 12, No. 2.

Manku, "A comparison of GLC and HPLC methods for determining fatty acid composition of evening primrose and soybean oil," J. Chromatographic Science, 1983, pp. 367-369, vol. 21.

Rasig et al., "Extraction of oils of hemp seed and analysis of the content of fatty acids in hemp oil," SOFW Journal, 1999, pp. 16-18, vol. 125, No. 1.

The Notice of References cited in U.S. Appl. No. 11/010,792, dated Dec. 1, 2010.

* cited by examiner

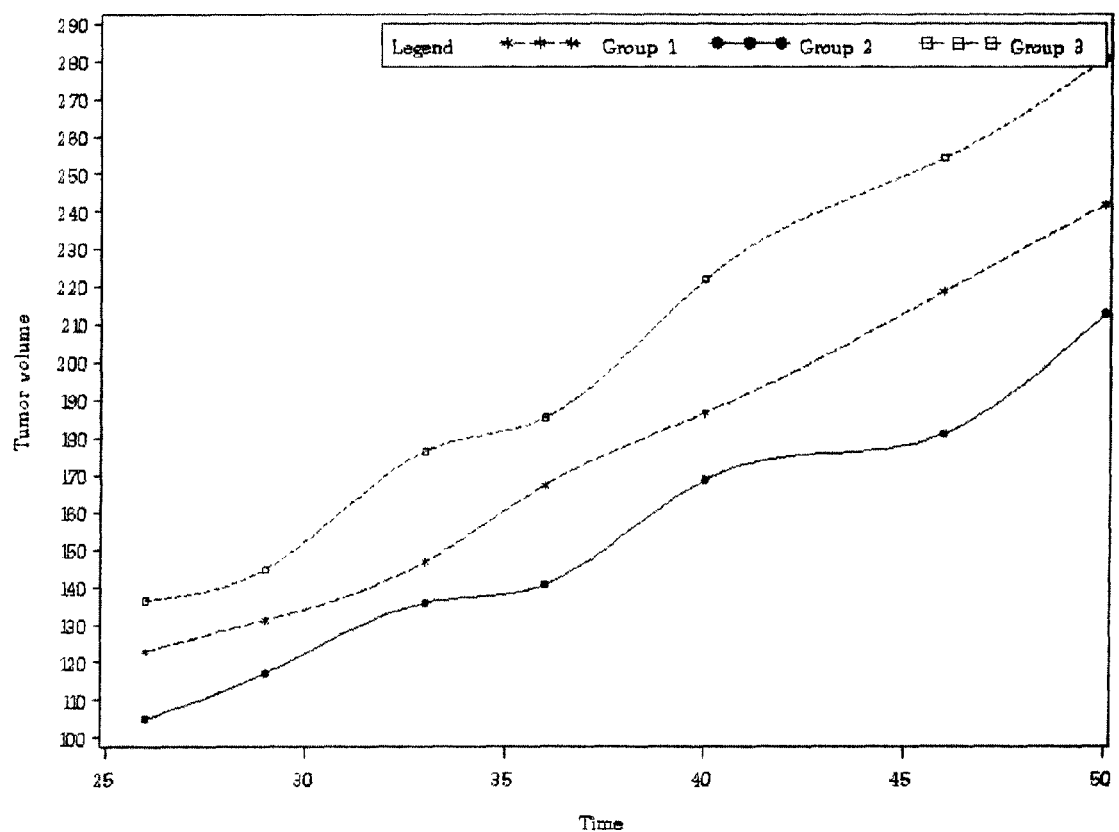

MEDICAMENT FOR TREATMENT OF CANCER AND OTHER DISEASES

CROSS REFERENCE TO RELATED APPLICATIONS

This application is a Continuation in part of U.S. patent application Ser. No. 11/010,792, filed Dec. 13, 2004, the contents of which are incorporated herein by reference.

BACKGROUND OF THE INVENTION

1. Field of the Invention

The invention relates generally to a medicament for the treatment and prevention of cancer. In other aspects, the invention relates to methods of treatment for cancer and other diseases, including vascular diseases.

2. Description of the Related Art

Pre-1920 cancer rates were so low they were virtually non-existent. Cancer rates at that time were a mere 3%-5%, and today, the cancer rate is close to 40%, and is expected to grow 50% worldwide by 2020. Between 1973 and 1999, deaths from cancer increased by 30%, from 17.7% to 23% of the population, according to the Centers for Disease Control (CDC). This does not include the one million new cases of skin cancer each year. "SEER Cancer Statistics Review 1973-1999," L. A. G. Ries, M. P. Eisner, C. L. Kosary, B. F. Hankey, B. A. Miller, L. Clegg, B. K. Edwards, eds., National Cancer Institute, Bethesda, Md. (2002), quoted in "The Stop Cancer Before it Starts Campaign-How to Win the Losing War Against Cancer," by Samuel S. Epstein, M.D., at www.preventcancer.com, p. 5. Genetics and other areas of study have fallen short on their promise of prevention and cure.

Nobel Prize-winner Otto Warburg and others have conclusively showed that all cancer cells have a damaged respiration (oxygen usage). This finding is so prevalent that he called this irreversible change cancer's "prime cause." Warburg also showed that oxygen impairment of a 35% decrease from normal causes cells to become cancerous. To the inventor's knowledge, no one has taken the approach to solving cancer by utilizing Warburg's findings of increasing cellular oxygenation by the particular method disclosed herein. A proper combination of "parent" EFAs (essential fatty acids) from EFA-containing oils, in ratios based on actual body tissue and hormonal usage (in vivo) has not been used. Otto Warburg's research clearly showed lack of cellular oxygen is the "prime cause" of cancer, but its practical application was unknown.

The inventor contends that the cause of decreased cellular oxygen to transference must be directly related to something that changed post-1920. Of all the possibilities that are universal to everyone regardless of income, race, or nationality, only food-processing is universal enough in nature to allow a 40% cancer rate in this short period of time. Food processing is the unique universal condition that affects all races, socioeconomic classes, and nationalities. Even the finest restaurants use processed food to some extent. EFA-deficiency was first described in 1929 by Burr and Burr (Burr G O, Burr M O: "A new deficiency disease produced by the rigid exclusion of fat from the diet," J Biol Chem 82:345-367, 1929)

Warburg, himself, wrote:

" . . . The era in which the fermentation of the cancer cells or its importance could be disputed is over, and no one today can doubt that we understand the origin of cancer cells if we know how their large fermentation originates, or, to express it more fully, if we know how the damaged respiration and the excessive fermentation of the cancer cells originate . . . . " (Warburg, Otto, "On the Origin of Cancer Cells," Science, Volume 123, Number 3191, February 1956, director of the Max Planck Institute for Cell Physiology, Berlin-Dahlem, Germany and Otto Warburg, Director, Max Planck-Institute for Cell Physiology, Berlin-Dahlem and "The Prime Cause and Prevention of Cancer with two prefaces on prevention": Revised lecture at the meeting of the Nobel-Laureates on Jun. 30, 1966 at Lindau, Lake Constance, Germany, The Second Revised Edition published by Konrad Triltsch, Würzburg, Germany, 1969. English Edition by Dean Burk—National Cancer Institute, Bethesda, Md., USA. The 1955 article is based on a lecture delivered at Stuttart on 25 May 1955 before the German Central Committees for Cancer Control. Translation was by Dean Burk, Jehu Hunter, and W H Everhardy at the National Institutes of Health (USA).

Cancers occur in a variety of organs. As Warburg makes so clear, there has to be a prime (singular) cause that could produce cancer in various cells and organs. Only food processing is the single cause that produces something that could cause a cancer virtually anywhere in the body. A prime mechanism to prevent oxygen transfer and cause cancer is via a transfat or processed oil (Baumann, C. and Rusch, H., American Journal of Cancer, 1939, 35:213-221). Transfats along with cross-linked and polymerized bonds resulting from oil processing are in many foods that we all eat. These are required in modern food processing to increase shelf life. Transfats and processed oils containing cross-linked and polymerized bonds are known to inhibit oxygen transfer because a transfat or other commercially processed oil, like margarine or most supermarket cooking oils, never goes bad or takes a significant amount of time to become rancid due to oxidation. They won't react (oxidize) with anything. There is little or no oxygen transference. Compare this with a piece of steel that is placed in air. Within a short period of time, the steel will develop rust due to an oxidation (oxygen transference) reaction. Or, place a piece of fish in air. Without refrigeration, the fish's oils quickly oxidize, causing that awful "fishy" smell.

Abnormal amounts of fat and LDL cholesterol in the blood may also lead to the narrowing and hardening of the arteries and cause blockage of the arteries, thus increasing the risk of getting cardiovascular diseases.

Cardiovascular diseases are the world's largest killers, claiming 17.1 million lives a year. Tobacco use, an unhealthy diet, physical inactivity and harmful use of alcohol increase the risk of heart attacks and strokes.

Cardiovascular diseases include coronary artery disease (CAD) and cerebral vascular disease. Coronary artery disease, also called ischemic heart disease, is caused by the hardening or thickening of the walls of the blood vessels that go to the heart. Cerebral vascular disease is caused by narrowing, blocking, or hardening of the blood vessels that go to the brain or by high blood pressure, and affects blood flow to the brain, leading to strokes and transient ischemic attacks (TIAs). Heart failure is a chronic condition in which the heart cannot pump blood properly. Narrowing or blockage of blood vessels by fatty deposits in the legs causes peripheral arterial disease (PAD), which in turn increases the chances of a heart attack or stroke.

Widespread food processing of oils commenced in 1911 with the patenting of CRISCO® and continues currently. This chemical process is often termed hydrogenation, and results in transfats and other unnatural molecules, which ruins the oxygenating ability of the polyunsaturated oils. Hydrogenated oils and other modified (including cross-linked) oils are known to cause cancer among other ailments, although the specific reason has not been confirmed by consensus. The processing of commercial oils causes numerous chemical reactions (cross-polymerization, etc.) which stop the oxygen transfer of EFAs. Lastly, there may be only 1%-2% transfats from the oil processing but in absolute numbers there will be an order of magnitude of some $1\times10^{21}$ molecules per tablespoon of oil (The molecular weight of a triglyceride is approximately 1,000. A liter of oil contains approximately 1,000 grams, and therefore, $6\times10^{23}$ molecules. There are approximately 100 Tablespoons per quart and therefore there is on the order of $10^{21}$ defective molecules per tablespoon of processed oil. The body contains about 100 trillion cells ($1\times10^{14}$ cells); an overload potential of $10^5$ defective EFAs/cell. Therefore, the potential for damage by them, either used integrally in the cellular structure, or in biochemical reactions, is highly significant.

Prior art attempts to provide an acceptable cancer medicament have focused on either significant use of omega-6 derivatives, a greater amount of parent omega-3 compared to parent omega-6 (such as U.S. Pat. No. 6,159,507, Igarashi, Dec. 12, 2000 suggests) than the present invention, or the use of omega-3 derivatives, such as fish oil, or requiring high dosages of the drug. Other attempts have relied upon physiologically (unreasonable) amounts of the drug to accomplish cancer-suppressive effects, such as the method described in U.S. Pat. No. 5,457,130 (Tisdale et al., Oct. 10, 1995) whereby a mouse is treated with 100 ul active ingredients or the extremely high dose that U.S. Pat. No. 5,766,571 (Ceriani et al., Jun. 16, 1998) requires.

Certain natural oils that do contain a desirable ratio of parent omega-6 EFAs to parent omega-3 EFAs are not preferred for use in cancer prevention. Canola oil, for example, (rape seed—of the mustard family of plants) is not preferred due to concerns over genetic modification, cross-breeding issues, and concerns of inherent toxicity. Soy oil is not preferred because of potential endocrine disrupting issues, etc. Hemp oil (from the Cannabis/marijuana plant) is not preferred due to potential THC (Tetrahydrocannabinol) issue and other concerns. Further, hemp oil is not derived from a true seed, but from an "achene," a tiny nut covered by a hard shell. The use of fish oil is not preferred in supra-physiologic amounts because it is "derivative-based" omega-3, and often has contamination issues and other concerns. Molecular distillation processing still leads to problematic boiling of the fish oil. Other natural oils, whose effectiveness against cancer has not been proven, may be excluded as well. The same concerns apply for use in treating and preventing vascular disease.

The present invention is directed to overcoming the problems of the prior art.

SUMMARY OF THE INVENTION

The present invention is generally directed to an improved medicament for the treatment and prevention of cancer and cardiovascular diseases in subjects in need thereof. The subjects may be adults or young adults (adolescents). In other aspects, the present invention provides an improved method for treatment of cancer, as well as heart disease or other illnesses. In currently preferred embodiments, the medicament is created by combining a plurality of unrefined and chemically unprocessed oils containing "parent" omega-6 and "parent" omega-3 essential fatty acids or their analogues so that the combination contains a ratio of parent omega-6 to parent omega-3 within a particular range. Preferably, the ratio of omega-6 to omega-3 in the medicament ranges from greater than 1:1 to about 5:1. More preferably, the ratio is in the range of about 2:1 to about 4:1. Most preferably, the ratio is about 2.6:1. Preferably, at least 50% of the composition comprises linoleic acid (LA) and α-linolenic acid (ALA) in a LA/ALA ratio that is greater than 1:1 and less than 5:1. More preferably, at least 60% of the composition comprises linoleic acid(LA) and α-linolenic acid (ALA) in a LA/ALA ratio that is greater than 1:1 and less than 5:1. Even more preferably, at least 65% of the composition comprises linoleic acid (LA) and α-linolenic acid (ALA) in a LA/ALA ratio that is greater than 1:1 and less than 5:1. The medicament helps prevent cancer and cardiovascular diseases by increasing oxygenation of the body tissue. The medicament also helps cure cancer by increasing oxygenation of the existing cancer and minimizing its growth.

The anti-cancer blend of the present invention contains more "parent" omega-6 than omega-3 in the preparation of a medicament comprising unrefined and chemically unprocessed oils from various seeds. The medicament may be administered orally in the form of a tablet, powder, capsule, syrup, minicapsule, etc., or topically in the form of lotion, cream, gel or emulsion, for preventing cancer and cardiovascular diseases by increasing oxygenation to the tissue (via membrane oxygen transfer, etc.). It will, therefore, both prevent cancer and cardiovascular diseases and minimize existing cancer and cardiovascular diseases by increasing oxygenation above this threshold of impairment.

In preferred embodiments of the present invention, no more than 12% of the total EFA mixture constitutes omega-6 derivates, such as GLA (gamma-linolenic acid). Also in preferred embodiments, no more than 40% of oleic acid is used since oleic acid is a nonessential acid that the body makes on its own, as needed. In even more preferred embodiments, the composition comprises no more than 25% of oleic acid.

In further preferred embodiments, an antioxidant is added to the medicament to reduce the potential for premature oxidation. Adulterated or chemically processed vitamin E is not preferred because the extraction methods and oil carriers can have the same negative effects as processed EFA-containing oils. It has been noted that organic extra virgin coconut oil has antioxidant properties. This is demonstrated because of the fact coconut oil can be not refrigerated for a year and its inherent EFAs don't oxidize (turn rancid). Coconut oil is the preferred oil to lessen oxidation.

In preferred embodiments, the medicament of the present invention may be administered to an adult or young adult (adolescent) in need thereof as an ingestible liquid form, or in solid form, such as an oil-based gel capsule, a tablet, or a powder. Administration of the medicament to infants and children under the age of 10 is strongly not recommended. Therefore, the medicament cannot be administered in the form of an infant formula. In a further embodiment, the medicament may be administered as a topical ointment for treatment of cancer on skin.

BRIEF DESCRIPTION OF THE DRAWINGS

For detailed understanding of the invention, reference is made to the following detailed description of the preferred embodiments, taken in conjunction with the accompanying drawing.

FIG. 1 is a chart illustrating measured differences in tumor volumes between groups of mice from 26 to 50 days after tumor implantation.

DETAILED DESCRIPTION OF THE PREFERRED EMBODIMENTS

The invention provides a greatly improved method of treatment for cancers and cardiovascular diseases. The term "treatment," as used herein is intended to refer to medication for treatment of active cancers and cardiovascular diseases, as well as preventative treatment for potential cancers and cardiovascular diseases. What inhibits respiration and its prevention in the cell is the basis of this invention. Specifically, the present invention solves a direct cause of oxygen inhibition—a lack of sufficient parent omega-6 and parent omega-3 in the cell and cell membrane. This lack is caused by food processing either hydrogenating the oils, destroying EFA functionality, removing the EFA containing oils, or adulterating them by heating, and in part or altogether, with preservatives which curtail oxygen transfer.

Omega-6 and 3 as Used By the Body In Vivo

There are 2 essential fatty acids that the body cannot make on its own that must come from food; parent omega-3, termed alpha-linolenic acid, and parent omega-6, termed linoleic acid. Because of the need for food processors to have long shelf-life, these essential oils are often highly adulterated (preserved) and biochemically ineffective and harmful when ingested in the body. The present invention focuses on these oils' anti-cancer properties because of their high tissue oxygenating ability. Much current focus has improperly been on omega-3 alone; in particular, from fish oil. This line of research is incomplete and not in accordance with how the body uses these oils because there is much less parent omega-3 in the tissues as compared with omega-6. This "dual approach" utilizing both oils in parent form, in one way, distinguishes this invention from others. The more common singular EFA approach concentrating on omega-3; in particular, their derivatives and not the parents, while working to some extent in vitro (outside the body) is incomplete and often highly ineffective when in vivo results are required. Although the following experiments were conducted using a formulation including higher amounts of saturated fat, omega-6 derivative (GLA), and monounsaturated fat, than parent EFAs, these fats are all nonessential—the body manufactures them (the GLA from the parent omega-6) and the invention's results are not from their inclusion. The medical textbook article quoted from below makes it clear that omega-6 and omega-3 fatty acids in combination [in vivo] at low doses were more effective than omega-3 alone at a high dose. The following is the pertinent phrase: " . . . [There is a] synergistic effect of n-6 [omega-6] and n-3 [omega-3] fatty acids at low doses which is greater than the effect of high doses of n-3 fatty acids alone." (Prostaglandins in the Cardiovascular System, pages 151-156, 1992.)

Experimental Procedure #1

The metabolism of n-6 and n-3 PUFAs in rats and mice are similar to humans. (Lands, W. E., et al, Lipids, Vol. 25(9), 1990, pages 505-516.) Therefore, studies in mice would be predicted to be similar in humans. Regardless, one must be always aware that mice are not humans. For this reason, many drugs do not work as well in humans as in animals, if at all. Because this drug was designed for humans and their specific "parent" omega-6/-3 tissue ratios, we would therefore expect human results to be significantly better than results in mice.

Two very different laboratory experiments were conducted. The in vitro was unsuccessful and the in vivo both highly successful and significant.

The in vivo test was conducted by PhenoPath Laboratories in Seattle, Wash. To access the death rate in vitro by application of this formula ZR-75, breast carcinoma cells (from ATCC) were grown both with and without the fatty acid application. Medicament concentration was 725 mg/1.25 ml=580 mg/ml and diluted with ETOH for a 10 mg/ml final concentration of medicament. The final overall application was 20 ug/ml delivery to the cells. Total cell counts per plate were $2.5 \times 10^6$ in both cases. Rate of death from fatty acid application was then determined vs. the control given no fatty acids. Although others have shown a positive result with merely adding an EFA-based medicament to in vitro cancer cultures with 20 ug/ml killing human breast culture, ZR-75-1 breast carcinoma, (Michael Begin, et al "Differential Killing of Human Carcinoma Supplemented With n-3 and n-6 Polyunsaturated Fatty Acids," JNCI 1986: 77: 1053-1062), we observed no positive effect, nor did we expect one because the animal was not under the effect of hormonal influence by the animal's active biochemistry.

The cells were grown in RPMI-1640 per ATCC propagation indications. Cells were seeded into 24-well plates at a concentration of $2 \times 10^4$ cells/ml. The fatty acid was added to all wells of one of the plates at a concentration of 20 μg/ml. After a period of 6 days both of the plates were counted. Cells were lifted with trypsin and all of the wells in one plate pooled. The cells were spun down and counted with a hemacytometer using a trypsin blue exclusion method. A sample of cells was taken and live cells vs. dead cells counted for all eight squares of the hemacytometer. This was done three times and the numbers averaged. Ninety eight per cent (98%) of cancer cells were still alive in both treated and untreated mediums. That is, in vitro cell viability of both treated and untreated specimens were 98%.

This in vitro experiment showed no difference with treated vs. untreated cells. This lack of result was predicted because there are no hormonal influences outside of the body. The in vivo results were quite different.

We gave nude mice doses of the medicament that are proportionate to humans and not significantly more than anyone would ever naturally take like in the case of patent US 2002/0010211 A1, published Jan. 24, 2002. These experimenters gave the equivalent human dose of 10 g/day medicament. This invention uses a much more reasonable 4.3 g/day. Furthermore, we look to a more statistically significant tumor size inhibition of at least 20% reduction in growth after steady-state conditions have been reached after transplant.

Experimental Procedure #2

The medicament was given to the mice in this study only 5 days per week whereas in humans the dosage would be 7 days a week. Therefore, the results in humans would be expected to be of an even greater magnitude. Perry Scientific, located in San Diego, Calif. was chosen to conduct the in vivo study using nude mice. The breast cancer tumor strain of MDA-MB-435 Breast Cancer Line (supplied by PSI) was chosen for implantation in athymic nude mice. Cell line media was appropriate for the cell line. Cell line propagation by PSI was by standard in vitro cell expansion methods. The age of the mice was 4-6 weeks. Their vendor was Simonsen Laboratories, Gilroy, Calif. Prolab® 5P75 (#55875). Mouse Chow was used throughout. The medicament was added to their feedings. There was no replacement or substitution of any kind in feeding regimens. Three groups were used: Group 1 was pretreated with the medicament 2 weeks prior to tumor implantation. Group 2 was pre-treated with the medicament 4 weeks prior to tumor implantation. Group 3, the control, was not pre-treated. Treatment of all animals was by oral gavage, 5 days per week (M-F) until termination. 23 nude female mice were inoculated with $2.5 \times 10^6$ MDA-MB-435 breast cancer cells subcutaneously. Tumor volumes were monitored by caliper measurement twice per week. Animals were sacrificed at 50 days post tumor inoculation.

Group 3 consisted of 10 mice whereas both Groups 1 and 2 consisted of 5 mice each. Animals were acclimated for at least 3 days prior to initiation of dosing. The 3 extra mice were not required in the study.

Drug dosing was based on bodyweight measurements of the mouse. The human-based drug dose is 4,350 mg based on a 180-pound person. The EFA blend used was 50% organic evening primrose oil, 33.3% organic flax oil, 10.7% organic pumpkin oil, and 5.95% organic virgin coconut oil. This gives a "parent" omega-6/-3 was approximately 2.6/1.0. Organic crops have variation and there is always a variance from "table values."

Mice typically weigh 18-22 grams so we calculate 1 ul/mouse per day dosage. Final dosage form was 1 ul active with 99 ul of added organic virgin coconut oil (a highly saturated non-essential fat) allowing a 100 ul feed per each dosing day. The control animals were given 100 ul of pure coconut oil with no drug added. Prior to animal dosing the invention/coconut oil mixture was heated to room temperature and mixed to ensure adequate distribution of the drug in the vehicle. Garden of Life® brand organic extra virgin coconut oil, Jupiter, Fla., was used as the vehicle for each of the 3 Groups.

Tumor size was based on external caliper measurement of protruding tumor with the primary tumor excised and weighed at termination. Tumor volume was calculated twice each week based on the formula $\frac{1}{2}(a \times b^2)$, where b is the smaller of the two perpendicular diameters. All mice were used in the statistical analysis. None were selectively deleted. Because there are so many errors in reporting statistical analysis, (Gatz, Stanton A., Primer of Biostatistics, 5th edition, McGraw-Hill Medical Publishing, page 7, 2002) an independent expert in statistics (Alex Kiss) was selected for the analysis.

Statistical Analysis

A repeated measures analysis of variance was carried out to assess to differences in tumor volume between the three groups over time, focusing on the time period from day 26 and onwards (By Alex Kiss, Ph.D., Statistics Consult, Oct. 18, 2004.) The analysis showed both a significant difference between groups ($F_{2,119}$=4.06, p=0.02) as well as significant differences in the interaction between groups over time ($F_{18,119}$=2.21, p=0.006). The differences were strongest between group 2 and group 3 ($t_{119}$=−2.78, p=0.006) with group 2 having significantly reduced tumor volumes across the time period as a whole. The differences between group 1 and group 3 were not as strong across the whole time period of analysis ($t_{119}$=−1.52, p=0.13).

| Test of Group and Group by Time Differences | | | | |
|---|---|---|---|---|
| Effect | Num DF | Den DF | F Value | p-value |
| GROUP | 2 | 119 | 4.06 | 0.0196 |
| GROUP*time | 18 | 119 | 2.21 | 0.0059 |

| Group by Group comparisons | | | | | | | |
|---|---|---|---|---|---|---|---|
| Effect | GROUP | GROUP | Estimate | Standard Error | DF | T Value | p-value |
| GROUP | 1 | 2 | 22.0159 | 20.0856 | 119 | 1.10 | 0.2752 |
| GROUP | 1 | 3 | −26.3754 | 17.3946 | 119 | −1.52 | 0.1321 |
| GROUP | 2 | 3 | −48.3913 | 17.3946 | 119 | −2.78 | 0.0063 |

A univariate repeated measures analysis of variance is the most appropriate statistical device to determine whether a significant difference exists when looking at tumor volumes between groups over time. Analysis of variance is the test of choice when there are 3 or more groups of interest and the dependent variable is a continuous measure (as volume is in this case). The repeated measures analysis of variance, takes into account the fact that measures taking over time are not independent but dependent due to the fact that one subject (mouse) provides several measures, one at each time point. To account for this dependence, a repeated measures analysis of variance sets up a correlation design whereby a single subject's measurements are assuming to share some similarities and therefore not be treated as independent entities. The repeated measures analysis is far superior to running many separate t-tests for each time point. In addition to the above mentioned reasons, it is a single test with its usual associated Type 1 error rate of 5%. When running many independent tests, each of which has its own Type 1 error rate of 5%, you have increased your chance of a false finding. The larger the number of independent tests, the greater the chance of a false finding. Therefore in all circumstances it is beneficial to run a single test when possible to answer a research question as opposed to many separate tests.

TABLE 1

| Mean differences in tumor volumes between groups over 26-50 days. | | | |
|---|---|---|---|
| | Mean difference in decrease in tumor size | Standard Error | 95% Confidence Interval |
| Group 1 vs Group 3 | −26.38 | 17.39 | −60.46  7.70 |
| Group 2 vs Group 3 | −48.39 | 17.39 | −82.47  −14.31 |
| Group 1 vs Group 2 | 22.01 | 20.09 | −17.37  61.39 |

Discussion of Results

FIG. 1 graphically depicts measured tumor volumes among the three groups of test mice between 26 and 50 days following tumor implantation. Fifty days (50 days) of measurement was used after tumor implantation. Statistical results commenced after day 26 because this timeframe allowed all transient conditions, including hormonal disruption, of tumor implantation to subside. The 4-week pre-treat drug (Group 2) vs control was most significant as can be seen from the graph of FIG. 1. Every 4-week pre-treat drug group at this day 26 endpoint, the final endpoint (day 50), and every intermediate point was significantly less in size (growth) than the control. This same effect occurred with Group 1 although to a lesser extent than Group 2, as would be expected. This result clearly shows the drug's value increases with longer pretreatment. A logical conclusion from this result would be that the medicament is modifying the cell's internal structure, making it more cancer resistant. From Table 1 presenting Mean Differences we can see a −48.39 mean difference between Group 2 vs Group 3. This translates to a 24.1% decrease mean tumor volume with the medicament.

When results are analyzed after 40 or 50 days, we see over a 30% mean reduction in tumor size with Group 2 vs control Group 3. Although tumors in each group continued to grow, the significance of Group 2's effect was even more pronounced. Given that cancer develops very slowly in humans and given the cellular modifying capability evident looking at Group 1 and Group 2 in which both drug doses are identical and only the length of the pre-treatment phase differs, one could conclude that, given adequate pre-treatment with the drug, cancer would not ever normally occur in a human.

Group 3 (control) had a cancer tumor mean growth volume rate of 135 cc to 270 cc occurring over 24 days. Group 2 had the same doubling of growth volume rate, yet a difference in mean absolute size from 105 cc to 210 cc. Looking at the endpoint at the last 10 days (experiment's end) between Group 2 and 3 we see a growth volume of 42 cc vs 60 cc=18/42=42.8% decrease with the drug.

Two additional facts are most important: The results of experiment #2 were with mice treated during 5/7th of the week (5 out of 7 days), not daily as would actually occur of the weight proportional dosage a human would receive because the lab is closed 2 days a week. Furthermore, the medicament used with the mice was specifically designed for human's specific tissue structure based on tissue parent omega-6/-3 ratios along with a factor of how much of these parent EFAs are converted by the body into biological derivatives (Peskin, Brian S., "The Scientific Calculation of the Optimum Omega-6/-3 Calculation," Biosciology Publishing, Houston, Tex. 2004 (private paper)). Therefore, although the results in mice would be indicative of the result in humans, the results in humans should be significantly more pronounced than in mice.

A medicament prepared in accordance with the present invention has a combination of "parent" omega-6 and "parent" omega-3 containing oils (essential fatty acids) or their analogues within a particular range of ratios. The ratio of omega-6 to omega-3 in the medicament ranges from greater than 1:1 to about 5:1. More preferably, the ratio is in the range of about 2:1 to about 4:1. Most preferably, the ratio is about 2.6:1. Preferably, at least 50% of the composition comprises linoleic acid(LA) and α-linolenic acid (ALA) in a LA/ALA ratio that is greater than 1:1 and less than 5:1. More preferably, at least 60% of the composition comprises linoleic acid (LA) and α-linolenic acid (ALA) in a LA/ALA ratio that is greater than 1:1 and less than 5:1. Even more preferably, at least 65% of the composition comprises linoleic acid(LA) and α-linolenic acid (ALA) in a LA/ALA ratio that is greater than 1:1 and less than 5:1. The medicament helps prevent cancer and cardiovascular diseases by increasing oxygenation of the body tissue. This anti-cancer blend contains more "parent" omega-6 than omega-3 in the preparation of a medicament comprising unrefined and chemically unprocessed oils from various seeds. The medicament may be administered orally in the form of a tablet, powder, capsule, syrup, minicapsule, etc., or topically in the form of lotion, cream, gel or emulsion, for preventing cancer by increasing oxygenation to the tissue (via membrane oxygen transfer, etc.). The medicament will therefore both prevent cancer and minimize existing cancer by increasing oxygenation above this threshold of impairment as Warburg's experiments showed.

The key to preventing cancer lies directly with preventing cellular respiration from failing. The approach of the present invention utilizes combinations of organically grown and organically processed seed oils containing more of the parent omega-6 and to a lesser extent parent omega-3 EFAs in specific combinations (ratios) and minimizes damaging of cellular respiration because it keeps oxygen transfer high. The prior experiments were conducted using a formulation including high amounts of saturated fat from the coconut oil, omega-6 derivative (GLA), and monounsaturated fat, these fats are all non-essential—the body manufactures them (GLA is manufactured from parent omega-6).

The present invention is directed to solving a direct cause of this oxygen inhibition—a lack of sufficient parent omega-6 and parent omega-3 in the cell and cell membrane. This lack is caused by food processing either by hydrogenating oils, destroying EFA functionality, removing the EFA containing oils, or by adulterating them by heating, and in part or altogether, with preservatives which curtail oxygen transfer. Warburg wrote that:

Another method for destroying respiration is to use respiratory poisons. From the standpoint of energy, this method comes to the same result as the first method. No matter whether oxygen is withdrawn from the cell or whether the oxygen is prevented from reacting by a poison, the result is the same in both cases-namely, impairment of respiration from lack of energy. The first notable experimental induction of cancer by oxygen to deficiency was described by Goldblatt and Cameron in 1953 [Goldblatt, H. and Cameron, G., "Induced malignancy in cells from rat myocardium subjected to intermittent anaerobiosis during long propagation in vitro," J Exp Med. 1953 April; 97(4):525-52] who exposed heart fibroblasts in tissue culture to intermittent oxygen deficiency for long periods and finally obtained transplantable cancer cells, whereas in the control cultures that were maintained without oxygen deficiency, no cancer cells resulted. Any respiratory injury due to lack of energy, however, whether it is produced by oxygen deficiency or by respiratory poisons, must be cumulative, since it is irreversible. Frequent small doses of respiratory poisons are therefore more dangerous than a single large dose, where there is always the chance that the cells will be killed rather than that they will become carcinogenic.

Warburg, supra. This cumulative oxygen deficiency can be caused by a defect in EFA structure, often increasing over time, to varying degrees within various tissues.

Dr. Warburg and others showed in numerous experiments spanning many decades that a 35% lack of oxygen to the cell was always sufficient to induce cancer. The present invention focuses on the prevention and treatment of cancer by maximizing oxygen transport to the cell and not just to the bloodstream, such as experienced in an athlete. Because athletes still get cancer, oxygenating the blood is not sufficient for cancer prevention or treatment. This invention details one method to increase cellular oxygenation.

Proof of EFA-Based Effectiveness

There has been significant published experimental evidence of EFAs; in particular, many focusing on EFA-derivatives and not EFA-parents successfulness in vitro. Following are a sampling of them. See Eynard, A. R., et al., "Dietary Deficiency or Enrichment of Essential Fatty Acid Modulates Tumorigenesis in the Whole Body of Cobolt-60 Irradiated Mice," Prostaglandins Leukot Essential Fatty Acids March; 56(3):239-244, 1997) (indicating that general EFA deficiency will promote tumor growth); Purasiri, P., et al., "Effect of Essential fatty Acids on Natural Cytotoxicity in Patients with Colorectal Cancer," European Journal of Surgical Oncology 1995; 21(3):254-260)(indicating the need for general EFAs to be administered daily); (Eynard, A., "Is the Risk of Urinary Tract Tumorigensis Enhanced by a Marginal Chronic Essential Fatty Acid Deficiency?," Nutrition 1998 February; 14(2): 211-216); Jiang, W., et al., "Gamma Linolenic Acid Regulates Expression of Maspin and Motility of Cancer Cells," Biochemistry and Biophysics Research Communication 1997 Aug. 28; 37(3):639-644; Jiang W. G., "Regulation of cell adhesion, a central mechanism in the anticancer action of essential fatty acids." International Journal of Molecular Medicine 1998 March; 1(3):621-625; Eynard, A. R., et al., "Eicosatrienoic Acid (20:3 N-9) Inhibits the Expression of E-Cadherin and Desmoglein in Human Squamous Carcinoma in vitro," Prostaglandins Leukot Essential Fatty Acids 1998 December; 59(6):371-377; and Booyens, J., et al., "Dietary Fats and Cancer," Medical Hypotheses 1985 August; 17(4):351-362.

Overall, the literature suggests the clinical importance of EFAs generally in arresting cancer. However, the majority of these publications are from experiments conducted in vitro (outside the body). Furthermore, they utilize EFA-derivatives or EFA-based mixtures containing excessive omega-3-based compounds (including their derivatives). The aim of the present invention is to bring these high quality results in vivo (inside the body) with maximum effectiveness by utilizing optimum mixtures of parent omega-6 and parent omega-3 oils. To prevent or reduce oxidation, it is further preferred that the inventive blend of oils contain some antioxidant, such coconut (more preferred) or palm (less preferred). In addition, in preferred embodiments, the present invention seeks to optimally deliver these mixtures to the cells via periodic dosages of the compounds. The currently preferred period for dosage is daily.

Unadulterated EFA-Containing Oils are Not Abundant

Commercial food processing, using the process of hydrogenation and chemical processing, alters the EFAs in the ability to function properly, and are known to produce both cancer and heart disease. The food processors often require hydrogenation and preservatives to stop foods from oxidizing in order to have long shelf life and stability. Therefore, non-organically raised, chemically processed and refined oils are not used in this invention. Due to the presence of preservatives, parent omega oils which are cancer-preventing in their unadulterated form may become cancer-causing in their adulterated form. Chemically processed cottonseed oil via hydrogenation and other oxygen-transfer destroying methods have, for example, been associated with increased skin cancer. (Baumann, C. and Rusch, H., "Effect of Diet on Tumors Induced by Ultraviolet Light," American Journal of Cancer, 1939, 35:213-221.) Therefore, the converse of using chemically unprocessed EFAs should associate with decreased skin cancer. The medicament of the present invention contains organically raised oils which are chemically unprocessed and unrefined oils. By "chemically unprocessed and unrefined oils", it is meant that the oils do not undergo any processing, such as saponification, precipitation with ethanol, chemical filtration, acidification with hydrochloric acid and extraction with solvents, which cause degradation or alteration of the oils themselves, or a decrease in bioavailability or effectiveness, or a residue in the finished product.

In preferred embodiments, chemical pesticides, often used in growing, are to be excluded.

EFAS and Oxygen Attraction

Fatty acids double bonds strongly attract oxygen. That is why fish high in omega-3 series EFAs become rancid quickly. "When exposed to air [oxygen] natural fatty acids [EFAs] having two or more double bonds [omega-6 and -3] tend to undergo a complex process called autoxidation, in which molecular oxygen attacks a double bond . . . " (Short Course in Biochemistry, Lehninger, 1973, page 109). In the body, EFAs are therefore highly significant in allowing maximum transport of oxygen from the blood to cross the cell membrane. This crossing of the oxygen into the cell is a key point of this invention because simple oxygenation of the blood is not sufficient to prevent cancer; i.e., athletes get cancer. The oxygen must cross into the tissue. High levels of blood oxygen alone although beneficial to a limited degree in cancer prevention, as studied by Warburg, are insufficient to prevent tissue cancer from developing. This invention utilizes this finding and the fact that EFAs double bonds attract molecular oxygen (act as "oxygen magnets").

Decreased oxygen causes cardiovascular disease and stroke. The medicament of the present invention increases oxygen efficiency by a maximum of 100% over other fatty acids, such as monounsaturated oleic acid.

EFAs and Radiation Treatment

While undergoing radiation treatment for cancer, EFAs protective ability has been recognized. " . . . The results showed that EPA and DHA [both EFA derivatives] inhibited radiogenic transformations [radiation-caused cancer tumors] by 80-100% . . . . " "To achieve maximum protection against transformation EPA must be present continuously from the period before radiation treatment or just after. The presence of EPA, during the initiation phase of the transformation, i.e. in the first 2 weeks after exposure to radiation in a 6-week experiment was critical for effective inhibition of transformation." (Carmia Borek, Department of Physiology, Tufts University School of Medicine, Boston, Mass. from "Fatty Acids on Transformation of Cultured Cells by Irradiation and Transfection," by Mareyuki Takahashi, et al., Cancer Research 52 (Jan. 1, 1992): 154-162.)) While this was an in vitro study with EFA derivatives, preferred embodiments of the present invention are designed for maximum in vivo effectiveness by allowing the body to produce derivatives on an "as needed" basis from the parent EFAs.

Breast Cancer Rise Explained

"Women with high levels of alpha-linolenic [parent omega-3] acid in their adipose breast tissue have a 60% lower risk of breast cancer . . . . " and that this new finding "support a possible protective effect . . . . " (Bougnoux, P., et al., "Level of Alpha-Linolenic Acid [EFA] in Breast Tissue Inversely Linked to Breast Cancer Risk," European Journal of Cancer 2000; 36: 335-340) This study clearly shows significant in vivo anti-cancer results from a parent EFA (parent omega-3) in a specific area, breast tissue. It can be seen how essential the parent form of omega-3 is in producing a significant in vivo effect. Fatty tissue like the breast contains areas of 80-95% fat concentration. These fatty components of breast tissue require and should have high EFA concentrations, but because of modern food processing, they often don't. Oxygen deficiency in the breast tissue will be very significant. We can deduce that breast tissue would be a site of significant expected cancer site in women—and it is. Most breast cancer victims have few traditional "risk factors." EFA-deficiency should manifest highly in this area. There is so much lipid content, that a deficiency should manifest significantly here and it does. The present invention addresses and solves why this type of cancer has become so significant in its prevention and treatment.

High Blood Speed

Warburg stated that based on experiments, "[t]o prevent cancer it is therefore proposed first to keep the speed of the blood stream so high that the venous blood still contains sufficient oxygen; second, to keep high the concentration of hemoglobin in the blood . . . " EFAs (in particular, LA) have also been associated with a decrease in cholesterol regardless of saturated fat intake, i.e. an independent factor. "LA (parent omega-6) lowers cholesterol independently of displacing saturated fatty acids was shown in a study which LA was added rather than substituted. Despite the resultant high fat intake, LDL cholesterol fell." (Rassias, G., et. al, "Linoleic acid lowers LDL cholesterol without a proportionate displacement of saturated fatty acid," European Journal of Clinical Nutrition 1991; 45:315-320.) Medicaments in accordance with the present invention address this issue and "add" the LA without regard to other factors. There is no requirement to decrease another fat. Furthermore, it is known that parent is omega-6 keeps the blood platelets apart (less clumping) which makes parent omega-6 act like a natural "blood thinner" mimicking the drug sodium warfin. ("Eicosanoids [made from EFAs], other fatty acid metabolites and the vascular system: Are the present antithrombotic approaches rational?," Prostaglandins in the Cardiovascular System, 1992). EFAs, in particular parent omega-6, linoleic acid, also decrease blood pressure and the authors considered it important. (*Progressive Lipids Research;* 20:349-362, 1982) Lower systolic blood pressure implies less arterial blockage. This effect coupled with less platelet stickiness allows increased blood speed and hence maximally high oxygen content as Warburg requires.

GLA, an omega-6 derivative, is the basis for the body's most powerful natural anti-inflammatory, prostaglandin $PGE_1$. If functional parent omega-6 intake is lower or conversion to derivatives is impaired for any reason, the potential for inflammation increases, which may lead to atherosclerosis. This is why a preferred embodiment of this invention includes GLA.

A Statin-Like Effect

Similar to statins, EFAs help to prevent and minimize vascular disorders so that blood flow stays fast and highly oxygenated. "Statins and polyunsaturated fatty acids have similar actions." "In view of the similarity of their actions and that statins influence essential fatty acid metabolism, it is suggested that EFAs and their metabolites may serve as secondary messengers of the action of statins . . . . " (Das, U. N., "Essential Fatty Acids as Possible Mediators of the Action of Statins," Prostaglandins, Leukotrienes and Essential Fatty Acids, Vol. 65, No. 1, pages 37-40, July 2001)

While the primary utility of the present invention is cancer-prevention, it is also highly useful in the prevention and treatment of cardiovascular disease. Prostaglandins of the omega-6 series ("parent" omega-6 derivatives the body manufactures) found to reduce blood pressure and a strong inhibitory effect of clogged arteries. (Iacomo, J. M., et al., "The role of dietary essential fatty acids and prostaglandins in reducing blood pressure," *Prog Lipids Research;* 20:349-362 (1982).)

Lipids are the medium for biochemical gas transfer so that the gas can readily enter the cell; i.e., oxygen transfer. "Gases such as oxygen, $CO_2$ and nitrogen—small molecules with little interaction with solvents—readily diffuse through the hydrophobic regions of the membrane" (Harper's Illustrated Biochemistry, $26^{th}$ edition, page 418) "There are 2 classes of essential fatty acids (EFA); the linolenic (n-6) and linolenic (n-3). They are required for glycerophosphatides (phospholipids) of cellular membranes." (Sinclair, H. M, "Prevention of coronary heart disease: the role of essential fatty acids," Postgrad Med J 1980 August; 56(658):579-84) EFAs are in the cellular membrane of all tissues. "In the presence of oxygen, polyunsaturated fatty acids are susceptible to a non-enzymatic process known as autooxidation or peroxidation [reacting with oxygen]. It occurs both outside the body, where it is responsible for rancidity, and in vivo. The basis for this susceptibility is the relative ease with which a hydrogen atom can be abstracted from the methyl group between the double bonds of the polyunsaturated fatty acid [EFA]." (Principles of Medical Biochemistry, pgs. 377-378) This shows that EFAs are highly oxygen reactive. From another medical textbook it is noted that, "Essential fatty acids [EFAs] are found in the structural lipids of the cell, often in the 2 position of the phospholipids, and are concerned with the structural integrity of the mitochondrial membrane" (Harper's Illustrated Biochemistry, $26^{th}$ edition, page 191). Once again, here is more confirmation of the structural importance of EFAs in the cell membrane. "Therefore, a high content of unsaturated fatty acid [EFAs] residues in the membrane lipids makes the membrane more fluid." ("Principles of Biomedical Chemistry," 1998, page 226) More fluidity means easier oxygen and other biochemical transfer because a saturated fat is not fluid and can accommodate little nutrient (including oxygen) transfer. It is well-known even in the non-medical texts that the fatty acid chains' double bonds capture oxygen (Robert Erdman, Ph.D. and Merion Jones, *Fats That Can Save Your Life*: The Critical Role of Fats and Oils in Health and Disease, 1995, pg. 88). "Deficiency of EFA in experimental animals causes . . . [among other things] uncoupling of oxidation (use of oxygen) and phosphorylation." (Sinclair, H. M., "Essential fatty acids in perspective," Hum. Nutr. Clin. Nutr. 1984 July; 38(4):245-60) Both of these processes are required for maximization of energy production in the mitochondria (ATP) and elsewhere. Lack of EFAs is shown to impede the use of oxygen. The important use of EFA-based membrane lipids can't be stressed enough. "Functionally and structurally, the components of the respiratory chain are present in the inner mitochondria) membrane as four protein-lipid respiratory chain complexes . . . . " (*Harper's Illustrate Biochemistry*, pg 93)

Oxygen and Free-Radicals

There is a belief that PUFA (polyunsaturated fatty acids) should be minimized because of a possible adverse effect of creating problematic cancer-causing free-radicals. This is false. Although there is this potential caused by the superoxide anion free-radical, it is rendered harmless in the body via the enzyme superoxide dismutase. Therefore, oxidation damage is not a significant issue that could lead to cancer instead of preventing cancer (Harper's Illustrated Biochemistry, $26^{th}$ edition, 2003, page 90). Furthermore, "EFAs are very easily peroxidized in air, but vitamin E protects against this." (Sinclair, H. M., "Essential fatty acids in perspective," Hum. Nutr. Clin. Nutr. 1984 July; 38(4):245-60). Vitamin E (alpha tocopherol) is naturally occurring in the oils themselves (natural antioxidant) which further protects against oxidation. Additionally, the body's own enzyme, which it manufactures, called superoxide dismutase (SOD) serves this anti-oxidant function, too.

Research Shows EFA Mediated Cellular Activity Decreases Cancer

Begin, Michele, "Differential Killing of Human Carcinoma Cells Supplemented With n-3 and n-6 Polyunsaturated Fatty Acids," JNCI, Vol. 77, No. 5, November 1986 discusses how EFAs selectively killed cancer cells in vitro [outside of the body]. Both ALA and LA (the parent EFAs) accomplished this result. The study notes that "[s]everal lines of evidence suggest that EFA metabolism is an important target in the complex metabolic changes that lead to, or are associated with, cancer. Neoplastic tissues exhibit outstanding differences in the metabolism of lipids from normal cells. An elevation in distinct ether lipids and a decrease in PUFA (polyunsaturated fatty acids) levels are major biochemical abnormalities that have been strongly correlated with cell transformations, tumorigenicity, and metastasis." This 1986 National Cancer Institute article clearly shows how EFAs in vitro are critical to cancer prevention and treatment, but they didn't know how to influence the metabolic pathway. This invention directly and specifically addresses these metabolic pathways in vivo.

Influence of EFA Diet Directly on Cellular Membrane Content

"The plasma membrane lipid composition in L1210 murine leukemia cells was dependent upon the type of fat fed to the host animal." (Burns, C. P. et al., "Effect of Modification of Plasma Membrane Fatty Acid Composition on Fluidity and Methotrexate Transport in L1210 Murine Leukemia Cells," Cancer Research 39, 1726-1732, May 1979). Later in the publication, it is stated that "The plasma membrane fraction prepared from the cells grown in mice fed the polyunsaturated sunflower oil [high in parent omega-6] diet contained almost 2-fold more polyenoic fatty acids and 34% more unsaturated bonds than those prepared from cells grown in mice fed the saturated fat-rich diet." This clearly shows the influence of EFAs in the diet and how they directly influence specific proportions of EFA-based cell membrane structure. This invention makes use of this fact by including more parent omega-6 than other inventions in this area because parent omega-6 is the predominant EFA in most tissue (aside from brain and central nervous system which has a high preponderance of derivatives, yet minimal percentage by tissue weight).

EFA Absorption Through the Skin

There are currently in excess of 1 million new skin cancer cases each year. Dermatologists often blame the sun. This reasoning is inconsistent with cultures that spend much time exposed to the sun and do not develop skin cancer. In addition to efficacy via ingestion, the medicament of the present invention is also of practical use to decrease skin cancer via topical application. EFAs are absorbed through the skin and into the cellular membrane. "Collins et al. have shown that parenteral administration of linolenic acid (as an emulsion of soybean lecithin) partially restores the abnormal serum lipids . . . ." "These data show that when vegetable oils were applied to the skin of EFA-deficient patients there was penetration and incorporation of their constituent fatty acids, into structural lipid of the epidermis. As the oils were triglyceride forms of the fatty acids, it is clear that they were actually metabolized by the skin (hydrolytic cleavage followed by acylation of lecithin). This is of particular significance in the treatment of the EFA-deficiency syndrome in that the abnormally low levels of cutaneous linoleate may be rapidly restored by cutaneous application." " . . . [W]e have shown that the cutaneous route is an important means of introducing essential fatty acids in the body when intestinal absorption is not possible. Also, the applied oil is metabolized by the skin and linolenic acid is incorporated into structural lipid." (Prottey, C, et al., "Correction of the cutaneous manifestation of essential fatty acid deficiency in man by application of sunflower-seed oil to the skin," The Journal of Investigative Dermatology, 64:228-234, 1975) This finding completes this invention's claim to both prevent and treat skin cancer as caused by EFA-deficiency.

In Vitro vs. In Vivo Effectiveness

It is well-known that positive in vitro (outside the body) results do not necessarily translate to in vivo results (in the body). That is why a key point is to focus on the "parent" EFAs so that the body makes the "derivative" EFAs as required. Many prior art experiments have used in vitro tests with comparatively significantly larger doses of derivatives than the body could ever manufacture on its own, regardless of how much EFA-derivative containing oils were ingested. This invention's approach is much more biochemically consistent with the actual metabolism of the body.

It is often assumed that all (or most of) the "parent" EFAs are converted to "derivatives," such as prostaglandins (cellular hormone-like substances). This is incorrect. "The role of essential fatty acids [EFAs] in membrane formation is unrelated to prostaglandin [EFA-derivative-based] formation." (Harper's Illustrated Biochemistry, 26$^{th}$ edition, page 193) This shows that a significant amount of "parent" EFAs stay in the cell membrane and are not converted into derivatives because only EFA derivatives are used in prostaglandin production. A misconception is that this conversion occurs to a higher degree than it actually occurs in the human body. "I have some difficulty with the statement on the need to reduce LA (parent omega-6) of the diet because 'This is necessary to reduce adverse effects of excess of arachidonic acid (AA—an EFA derivative) and its eicosanoid products.' Linking LA and AA in this way also implies a direct conversion of LA to AA, which is not the case. In fact, a very high dietary LA will reduce membrane AA. Also, I have some difficulty with the concept of a unitary ratio when there is clear disunity in the biological activities of the different parent and LCP (long chain polyunsaturated) EFAs. Hence the concept of omega-6/-3 ratios based on activity equality between omega-6 and -3 does not reflect the biological reality." (Crawford, M. A., "Commentary on the workshop statement. Essentiality of and recommended dietary intakes for Omega-6 and Omega-3 fatty acids," Prostaglandins Leukot Essent Fatty Acids 2000 September; 63(3):131-4). More omega-6 than omega-3 is required in the diet, and this invention utilizes this concept. The major metabolic route of ALA (parent omega-3) in the body is beta-oxidation. ALA accumulates in specific sites in the body of mammals, and only a small portion of the dietary ALA is converted to DHA. Once again, confirmation that more parent omega-6 is used in tissue. (Sinclair, A. J., et al., "What is the role of alpha-linolenic acid for mammals," Lipids 2002 December; 37(12):1113-23). We see that little of the parent omega-3 is converted to derivatives; it is either used (oxidized) as fuel or used in its parent form in the tissue, and much less of it is used compared with omega-6. "Linoleic acid (LA) accumulates throughout the body of most mammals, whereas alpha-linolenic acid (ALA) is rarely found in those tissues to the same extent as LA." (Fu, Z. and Sinclair, A. J., "Increased alpha-linolenic acid intake increases tissue alpha-linolenic content and apparent oxidation with little effect on tissue docosahexaenoic acid in the guinea pig," Lipids 2000 April; 35(4):395-400) From "PUFA Newsletter" (www.fatsoflife.com) "Alpha-Linolenic Acid Conversion Revisited," by Norman Salem, et al. states "A recent article in the PUFA Newsletter indicated that in adult men and women the 'average estimated conversion of . . . alpha-linolenic acid to n-3 LC-PUFA metabolites and docosahexaenoic acid was 17.3±12.8 and 3.6±3.8 percent, respectively (mean+SD)'. This is likely to be an overestimate of the actual overall conversion rates for several reasons. We further see that more LA is in tissue compared to ALA which directly leads to the conclusion that much more LA than ALA should be consumed in the diet to maintain these ratios." We see even with this overly excessive estimate of the parent omega-3 derivative conversion that theoretically no more than 37% of them are converted to derivatives. The article makes the case that in reality only about 5% of the parent ALA is converted into derivatives. Pawlosky and others calculate less than 1% goes to derivatives. The article ends with "The best estimates of alpha-linolenic acid conversion to n-3 LC-PUFA are much smaller than those claimed . . . . " This is another reason why this invention specifies the parent omega-6 and 3 series with very little derivatives, and more omega-6 than omega-3. Using in vitro tests with significant amounts of derivatives is not consistent with how the body reacts to oral ingestion of the EFA-containing oils. It is drastically incorrect and any method based on this mistake in reasoning will not be maximally effective in protection and treatment against cancer. The present invention allows the body to convert the parent EFAs to derivatives "as needed" by the body. This invention allows maximum oral ingestion efficiency.

In currently preferred embodiments, the oils used in the medicament are organically raised and processed to insure potency and lack of toxicity. Ingested toxicity (carcinogens) leads to cancer. Because of pesticide and other added chemicals along with chemical processing of the oils themselves (boiling, etc.), many EFA-containing oil products have cancer-causing transfats and harmful preservatives in them which counteracts any inherent anti-cancer properties.

EFA Parent Omega-6/-3 Analysis

In preferred embodiments, the present invention is directed to a medicament having a minimum parent omega-6/-3 ratio from a low of greater than 1:1 to a maximum of 5:1 with about 2.6:1 being very effective. Fish oil and its main components, DHA and EPA, are not to be used because of their inherent anti-cancer and immune-suppressing properties when taken in supra-physiologic amounts, along with the fact that it is mainly derivative EFA-based; not parent EFA-based. The analysis is based on information contained in Brian Peskin's paper on the subject privately published in 2004 ("The Scientific Calculation of the Optimum Omega-6/-3 Ratio") which utilizes the following information (among analyzes from other sources) from the proceedings of the International Society for the Study of Fatty Acids and Lipids (ISSFAL) $4^{th}$ Congress, Jun. 4-9, 2000 in Tsukuba, Japan. The report regarding fish oil causing decreased immunity and decreased tumor killing is titled "Omega-3 Polyunsaturated Fatty Acids, Inflammation and Immunity," by Philip C. Calder, Institute of Human Nutrition, University of Southampton, Bassett Crescent East, Southampton, UK. " . . . [S]tudies indicate that at the levels used, fish oil [omega-3 derivatives] decreases a wide range of immune cell responses such as natural killer cell and cytotoxic T lymphocyte activities, lymphocyte proliferation and production of IL-2 and IFN-y (1,2) . . . " . . . Recent studies have indicated that relatively low levels of the long chain omega-3 fatty acids (EPA or DHA at a level of 44% of total fatty acids or 1.7% of dietary energy) are sufficient to bring about some of the suppressive effects [on the immune system], that dietary EPA and DHA [omega-3 derivatives] both inhibit lymphocyte proliferation, and that dietary EPA but not DHA inhibits natural killer cell activity. "Supplementation of the diet of healthy human volunteers with fish-oil-derived omega-3 PUFA (1.2-1.4 gm/day) results in decreased lymphocyte proliferation, decreased monocyte and neutrophil chemotaxis, decreased production of IL-1, IL-2, IFN-y, IL-6 and TNF, and decreased expression of MHCII and some adhesion molecules on the monocytes . . . " [all of which are very detrimental to the immune system]. "This decrease causes increased cellular bacteria and impaired tumor cell killing." This incredible finding that fish oil (note: all fish oil is composed of exclusively omega-3 derivatives) actually decreases immunity and increases the risk of cancer further illustrates the effectiveness of this invention's parent EFA blend with no harmful amounts of omega-3 derivatives.

Important Organ and Tissue EFA Ratios

It is necessary for us to study the EFA composition of various tissues and organs like the brain, skin, heart and muscle to discover the overall EFA requirement of the body. First, it is known from pathology studies that the brain and nervous system have a ratio of one hundred parts of parent omega-6 to one part parent omega-3 (100 to 1). In contrast, most organs contain a 4:1 omega-6/-3 ratio, and a key fact about muscle structure is that muscle contains from 5.5 to 7.5 times more omega-6 than omega-3, depending on the degree of physical condition. (Agneta Anderson, et al., "Fatty acid profile of skeletal muscle phospholipids in trained and untrained young men," American Journal of Endocrinological Metabolism, 279: E744-E751, 2000)

Extremely fit individuals require less omega-6 because their oxygen-transferring efficiency, including an increased number of cell mitochondria, is greater than in nonexercising individuals. But because most of us are not elite athletes, the average person requires an even greater amount of omega-6. So, on average, a muscle contains 6.5 times more parent omega-6 than omega-3 (a ratio of 6.5 to 1). And last, most other tissues in the body contain a 4 to 1 ratio of omega-6 to omega-3. These relationships are shown in the table below.

| Tissue | Ratio of Tissue Composition | |
|---|---|---|
| | Omega-6 (LA) | Omega-3 (ALA) |
| Brain/nervous system | 100 | 1 |
| Organs and other tissues | 4 | 1 |
| Muscles | 6.5 | 1 |

The next factor to consider is what percentage of body weight the various organs constitute. The brain and nerve-related organs make up only about 3% of body weight. The remaining organs, such as the heart, liver, skin and pancreas, make up approximately 9% of body weight. Muscle accounts for close to half of human body weight (50%).

| Tissue | Ratio of Tissue Composition | | Percentage of Total Body Weight |
|---|---|---|---|
| | Omega-3 (ALA) | Omega-6 (LA) | |
| Brain/nervous system | 1 | 100 | 3% |
| Organs and other tissues | 4 | 1 | 9% |
| Muscles | 6.5 | 1 | 50% |

Many nutritional writers state that simply because the brain has a 1 to 1 omega-6 to 3 ratio, a 1 to 1 parent omega-6 to 3 ratio makes the ideal supplement or the ideal to base ingestion of the medicament. But this analysis is wrong. It should be obvious from the second table above that the majority of our EFA-containing tissues and organs (per the above chart, 59% of body weight) require much more unadulterated omega-6 than omega-3 to function properly. Letting any tissues run short on these omega-6 EFAs, as will occur if you follow the most prevalent nutritional recommendations, leaves tissues significantly more susceptible to decreased cellular oxygen transfer (cardiolipin in the mitochondria, where the respiratory energy reactions take place, is comprised of significant parent omega-6) and hence a much greater risk of cancer development.

EFA Parent Omega-6 and Parent Omega-3 Compositions of Seeds

| Seeds | | Fatty acid percentage in oil | | | | | | |
|---|---|---|---|---|---|---|---|---|
| | | Polyunsaturated | | | Monounsaturated | Saturated | | |
| | Fat Content | LNA | LA | LNA + LA | | | | |
| Name | in Seed (%) | 18:3w3 (%) | 18:2w6 (%) | W3 + w6 (%) | 18:1w9 (%) | 18:0 (%) | 16:0 (%) | Total (%) |
| hemp | 35 | 20 | 60* | 80 | 12 | 2 | 6 | 8 |
| chia | 30 | 30 | 40 | 70 | — | — | — | — |
| kukui | 30 | 29 | 40 | 69 | — | — | — | — |
| flax | 35 | 58 | 14 | 72 | 19 | 4 | 5 | 9 |
| pumpkin | 46.7 | 0-15 | 42-57 | 57 | 34 | 0 | 9 | 9 |
| soybean | 17.7 | 7 | 50 | 57 | 26 | 6 | 9 | 15 |
| walnut | 60 | 5 | 51 | 56 | 28 | 5 | 11 | 16 |
| Wheat germ | 10.9 | 5 | 50 | 55 | 25 | 18 | 0 | 18 |
| evening primrose | 17 | — | 81** | 81 | 11 | 2 | 6 | 8 |
| safflower | 59.5 | — | 75 | 75 | 13 | 12 | — | 12 |
| sunflower | 47.3 | — | 65 | 65 | 23 | 12 | — | 12 |
| grape | 20 | — | 71 | 71 | 17 | 12 | — | 12 |
| corn | 4 | — | 59 | 59 | 24 | 17 | — | 17 |
| sesame | 49.1 | — | 45 | 45 | 42 | 13 | — | 13 |
| rice bran | 10 | 1 | 35 | 36 | 48 | 17 | — | 17 |
| cottonseed | 40 | — | 50 | 50 | 21 | 25 | — | 25 |
| rape(canola) | 30 | 7 | 30 | 37 | 54*** | 7 | — | 7 |
| peanut | 47.5 | — | 29 | 29 | 47 | 18 | — | 18 |
| almond | 54.2 | — | 17 | 17 | 78 | 5 | — | 5 |
| olive | 20 | — | 8 | 8 | 75 | 16 | — | 16 |
| avocado | 12 | — | 10 | 10 | 70 | 20 | — | 20 |
| coconut | 35.3 | — | 3 | 3 | 6 | 0 | 91 | 91 |
| Palm kernel | 35.3 | — | 2 | 2 | 13 | 0 | 85 | 85 |
| beech | 50 | — | 32 | 32 | 54 | 8 | — | 8 |
| brazil | 66.9 | — | 24 | 24 | 48 | 24 | — | 24 |
| pecan | 71.2 | — | 20 | 20 | 63 | 7 | — | 7 |
| pistachio | 53.7 | — | 19 | 19 | 65 | 9 | — | 9 |
| hickory | 68.7 | — | 17 | 17 | 68 | 9 | — | 9 |
| filbert | 62.4 | — | 16 | 16 | 54 | 5 | — | 5 |
| macadamia | 71.6 | — | 10 | 10 | 71 | 12 | — | 12 |
| cashew | 41.7 | — | 6 | 6 | 70 | 18 | — | 18 |
| neem | 40 | 1 | 20 | 21 | 41 | 20 | — | 20 |
| Borage | 60 | — | 38 | 38 | 16 | 4 | 10 | 14 |
| black current | 30 | 13 | 47 | 60 | 11 | 2 | 7 | 9 |

*Includes up to 2% GLA—Gamma Linolenic Acid (GLA)
**Includes 9% GLA, borage contains approx. 24% GLA, black current contains approx. 17% GLA.
***Includes up to 5% erucic acid
Source: Urasmus, Udo, "Fats That Heal, Fats That Kill," Alive Books, Vancouver Canada, 1993 ISBN: 0920470386

The table above provides a listing of parent omega-6 and parent omega-3 content for various seeds. In preferred embodiments, the medicament is made by combining two or more of the chemically unprocessed and unrefined oils listed in the above table to achieve the desired ratio of omega-6 to omega-3. However, the oils of hemp and rape (canola) are excluded from the potential combinations for reasons indicated previously Inherent in designing a composition for use in this invention, with actual seeds as opposed to fabricated chemical analogues, will be inherent additional naturally occurring ingredients that may be either superfluous or only minimally active in relation to this invention's prime method of action. For example, Evening Primrose Oil inherently contains approximately 9% Gamma Linolenic Acid—GLA, (the $1^{st}$ derivative of parent omega-6).

Suitable oils for the medicament of the invention include, but not limited to, chia, kukui, wheat germ, rice bran, cottonseed, olive, avocado, coconut, palm kernel, beech, brazil nut, pecan, pistachio, hickory, filbert, macadamia, cashew, neem, hemp, flax, pumpkin seed, soybean, walnut, evening primrose, borage, black currant, safflower, sunflower, grape seed, sesame, rape (canola), peanut, almond, and corn. The oils must be organically grown, chemically unprocessed and unrefined. Oleic acid (18:1w9) content is to be minimized in the medicament, and in the preferred embodiment the content of oleic acid in the medicament is less than 40% of the total mixture by weight. In even more preferred embodiments, the medicament comprises no more than 25% of oleic acid.

Although some strains of sunflower and safflower oils contain a high amount of oleic acid (approximately 70%-80%), in the medicament of the present invention only high linoleic acid content strains of sunflower and safflower oils are used, with oleic acid contents of less than 40% by weight. Preferably, the medicament contains no more than 10% of palmitic acid.

In preferred embodiments, a blend of six oils is used. Preferably, the blend contains safflower, sunflower, flax, pumpkin, evening primrose and coconut oil. In different embodiments, a blend of at least three oils is used, including evening primrose, flax and coconut oil.

Additional particular seed or nut oil may be included in the medicament of the invention. For oils containing a high amount of linoleic acid (LA), the selected oil must contain at least 30% LA by weight, with preferred oils containing an amount greater than 40% LA. Examples of oils enriched in LA include hemp, chic, evening primrose, safflower, sunflower, soybean, walnut, wheat germ, borage, black current, grape seed, kukui, pumpkin, cottonseed, corn and sesame.

Among the oils containing a high amount of alpha-linolenic acid (ALA), flax is preferred, as it contains 58% of ALA. Hemp, chia and kukui have also high proportions of ALA. These oils must be chemically chemically unprocessed, unrefined, unadulterated and "natural" or organically certified to ensure no potentially harmful additives like harmful pesticides are used in the growing of the seeds or nuts.

Additional factors should also be considered in choosing the appropriate oils for the medicament of the invention, i.e., for example, whether there is a long history of culinary use of the particular oil. As an example, hemp oil, although meeting the above guidelines for use in preferred embodiments of the medicament, would not be ultimately preferred because it does not have a long-term verified use as culinary edible oil. It is used for paint, varnish, detergent, and even diesel fuel, caulking, and cement, and for many commercial and industrial purposes other than food consumption, calling into question its use for human consumption. Likewise, soybean oil would not be ultimately preferred because of its potential endocrine disrupting effect. Soy oil also has many non-food commercial and industrial uses, calling into question its use in human consumption.

In preferred embodiments, a GLA-containing oil is to be used. Evening primrose oil, borage oil, black current, or other oils may be used, with evening primrose being the preferred oil because of its increased effect on PGE1 synthesis. Preferably, the amount of the GLA-containing oil in the composition is between about 5% and about 50%.

In preferred embodiments, an anti-oxidant, such as coconut or palm oil, is added to the medicament in an amount of approximately 5% of the total mixture, by weight. Preferably, the medicament comprises a blend of safflower oil, sunflower oil, evening primrose oil, pumpkin oil, and flax oil: 16.5% evening primrose oil, 34.5% flax oil, 16.5% pumpkin oil, 5.5% coconut oil, 13.5% sunflower oil, and 13.5% safflower oil. In other preferred embodiments, the medicament comprises 16.5% evening primrose oil, 33.0% flax oil, 22.5% pumpkin oil, 5.5% coconut oil, and 22.5% sunflower oil. In yet other preferred embodiments, the medicament comprises about 50% organic evening primrose oil, borage oil or black current oil, about 33.3% organic flax oil, about 10.7% organic pumpkin oil, and about 5.95% organic virgin coconut oil.

Calculating the Parent Omega-6 TO Parent Omega-3 Ratio

The medicament can, for example, utilize about 50 percent Evening Primrose Oil and about 50 percent flax oil. In addition, the medicament, in a further preferred embodiment can comprise a blend of about 50% organic primrose oil, about 33.3% organic flax oil, about 10.7% organic pumpkin oil, and about 5.95% organic virgin coconut oil. The omega-6/-3 ratio is calculated from the following. Total parent omega-6=0.81 gm EPO+0.14 gm Flax. Parent omega-3=0 gm EPO+0.58 gm FLAX. Assume 10 grams used of each seed for a 50/50 mixture gives 9.5 gm parent omega-6/5.8 gm parent omega-3 for an overall ratio of 95/5.8=1.64 parent omega-6/-3. This procedure is carried out to formulate the parent omega-6/-3 ratio. If other ingredients are added such as coconut oil, their parent omega content, if any, would be added. An allowance in dosage would be given for the weight that the inherent nonessential components took up. Follow this procedure to obtain the invention's required range of greater than 1/1 to 5/1 or less parent omega-6/-3. Chemically synthesized analogues can also be used.

Eicosanoids

There is widespread misunderstanding concerning these interesting substances that is responsible for widespread, yet incorrect, nutritional recommendations telling us to "take lots of omega-3" (usually in the derivative form from fish oil supplements). Eicosanoids are the body's cellular analogy to hormones. But unlike hormones, they work in the body with lightning speed and don't last long. Furthermore, they act locally in the cells and don't actually enter the bloodstream, because their function is so rapid. While the parent omega-3 and 6s are used throughout the body predominantly "as is," omega-3 and omega-6 derivatives are made into these eicosanoids after many biochemical modifications, on an "as needed" basis. For example, the eicosanoids made from omega-3 EFAs come from the EFA derivatives DHA and EPA (which your body makes from parent omega-3 EFAs "as needed"). Another example is the eicosanoids made from omega-6 EFAs—your body manufactures them by modifying arachadonic acid (which your body makes from parent omega-6 or takes from certain naturally occurring fats in proteins ready-made—if they aren't adulterated). $PGE_1$ eicosanoids are formed from parent omega-6 and are known from the medical textbooks to be anti-inflammatory and have significant immune-enhancing properties (*Smart Fats*, pgs. 27-30). We need to ensure that plenty of them can be made. Once again, this supports this invention's requirement for a preponderance of omega-6 in its formulation.

It is also vital to note that the omega-3 and omega-6 eicosanoids work together in a complementary manner. Neither is ever found alone in the body. For example, one increases blood pressure while the other decreases blood pressure. This required natural balance is another reason that the current nutritional recommendation to highly favor omega-3 derivative EFAs over omega-6 EFAs is harmful. Doing so drastically unbalances the biological system. Overdosing on omega-3 and/or its derivatives, can lead to profuse internal bleeding from eicosanoid overproduction. The bottom line is that both omega-3 and 6 eicosanoids are manufactured as needed from parent omega-6 and -3 EFAs and do not require our direct intervention. This reinforces the invention's solution to supply unadulterated parent omegas.

The Correct Supplement Calculation

What are safe and effective quantities of omega-3 and omega-6 EFAs for maximal anti-cancer anti-cardiovascular disease supplementation? As explained above, the western diet is estimated to contain an effective (still capable of oxygen-transference) ratio of a maximum of 6 to 1 parent omega-6 to parent omega-3. Additionally, we have seen that the majority of cells in the body require a ratio of at least 6.5 to 1 omega-6 to 3. The difference between the estimated good EFAs obtained in the diet and the cells' requirement is 0.5 parts of omega-6 that need to be supplemented at the most conservative basis. To this we will add an additional amount of omega-6 to allow the "good" omega-6 to effectively combat and overpower the "bad" omega-6 in the diet: for this purpose we will add from 1 to 2 parts "good" omega-6. Therefore, we conclude that we require supplementation with an additional 1.5 to 2.5 parts of good omega-6 for every 1 part of omega-3 to meet the body's needs. For greater ease in formulating supplements, and to remain conservative in our recommendation, we will round these figures and deduce that an EFA supplement should contain a ratio of from a minimum of slightly greater than 1:1 parent omega-6 to omega-3, at the lowest end, up to 5:1 parent omega-6 to 3, at the high end because oftentimes more omega-6-containing foods are consumed than assumed in this calculation and we must meet the requirement to overpower the ingested but adulterated omega-6 with an increased amount of chemically unprocessed parent omega-6. This is a very conservative estimate for dosage requirement and assumes consumption of the minimum amount of non-oxygen-transferring (non-functional) oils. Given the lack of processed oil oxygenation and the number of de-oxygenating molecules formed from the processing, the average person consumes much more than this amount. Therefore, even more of the medicament must be administered for effectiveness. Thus, up to a 5:1 ratio of parent omega-6/-3 is permissible.

Difference in Commercial Food's Processing of Parent Omega-6 and Parent Omega-3 Oils It is significant to note that few parent omega-3 oils are processed. Mainly, the omega-6 containing oils are processed because unlike parent or derivative omega-3, the omega-6 EFAs are used extensively in food processing, i.e., frying and baking, etc. This fact can be readily confirmed at the supermarket's cooking oil section. Most of the natural omega-3 containing foods are only minimally processed, if at all, negatively influencing oil degradation. Therefore, this critical fact must be understood when designing the medicament's parent omega-3 amount.

Pharmaceutical Presentation

Because EFA-containing oils oxidize quickly, the best capsule for them is one which minimizes oxygen transfer through the capsule. The Licap™ capsule's tight lattice structure made by the Capsugel™ division of Pfizer is best for this purpose although others may suffice, if required. For ointment for use in topical application, any number of base preparations will suffice. The main requirement is to inhibit oxidation of the oils and allow the base not to impede their effectiveness when used topically. The medicament can also be linked to a polysaccharide for ingestion such as described in U.S. Pat. No. 6,649,191 (2003-11-18, Karkalas, John and Tester, Richard).

Embodiments of the present invention are specific in their requirement for parent omega-6/-3 ratios and functional amounts, unlike other approaches that are quite general and overly broad, such as U.S. Pat. No. 5,763,484 (Horrobin, Jun. 9, 1998). Medicaments in accordance with the present invention act both as a cancer preventative and a cancer treatment to impede cancer from getting worse once one has contracted the disease. The medicament also prevents and reverses cardiovascular disease.

This invention relates to both cancer prevention and treatment while undergoing radiation and chemotherapy. Nobel Prize-winner Otto Warburg conclusively showed many years ago that all cancer cells have an impaired respiration. Back then, there was no significant practical application that worked. He and others, including senior officials at the National Cancer Institute (America) also showed that cancer was always induced by depriving tissue by 35% of its normal oxygen content.

EXAMPLES

This study was made using Digital Pulsewave Analyzer (DPA). The DPA provides information on arterial wall stiffness and determines the biological age of arteries in less than 3 minutes. This FDA approved, user-friendly, non-invasive device uses a finger probe to observe the changes in pressure, blood flow, velocity and profile throughout the whole pulse wave.

To evaluate the effect of the medicament on preventing and reversing cardiovascular disease, long-term and short-term studies were performed. Specifically the effect of the medicament was evaluated for (a) long-term use in subjects taking the medicament for an average of approximately 24 months; (b) short-term use in subjects taking the medicament for an average of approximately 3 months; and (c) in place of fish oil supplement in subjects who stopped taking fish oil supplement and replaced the fish oil supplement with the medicament for an average of approximately 3.4 months.

The subjects (all adults) were administered a standard dose of 2.9 grams (2,900 mg) of medicament daily, in both liquid and capsule form. The medicament was administered either all art once or split into 2 doses of 1450 mg each. The medicament contained either 16.5% evening primrose oil, 34.5% flax oil, 16.5% pumpkin oil, 5.5% coconut oil, 13.5% sunflower oil and 13.5% safflower oil, or 16.5% evening primrose oil, 33.0% flax oil, 22.5% pumpkin oil, 5.5% coconut oil and 22.5% sunflower oil. No differences between the two kinds of medicament were noticed in the results of the study.

During the trial the subjects did not change their diet or exercise habits. Healthy subjects as well as subjects with existing diseases such as diabetes or cardiovascular disease, took part in the trial. The only subjects excluded were those whose test parameters were out of range of the machine calling into question their validity' i.e., "pulse height" and "ventricular ejection times."

Long-term medicament results: There were 33 people who completed the study, using the medicament for timeframes of approximately 3 months-48 months. Half of the subjects used the medicament under two years and half used the medicament over 2 years and less than 4 years, the median being 2 years. There were 22 females and 11 males. Subjects were 35-75-years-old, with the median age being 62-years-old.

The subjects had their arteries studied with DPA and compared to accepted waveforms for age. The results are shown in the table below:

| Patient | Sex | Age | Biological Age | Visit Date | Type | Age of Arteries | Months of Treatment | Smoker | Additional Medications | Fish Oil Supplement |
|---|---|---|---|---|---|---|---|---|---|---|
| 1 | M | 64 | 57 | 16 Nov. 2009 | D | 71 | 36 | No | No | No |
| 2 | M | 68 | 33 | 20 Nov. 2009 | B | 46 | 36 | No | No | No |
| 3 | M | 53 | 35 | 05 Nov. 2009 | B | 59 | 48 | No | No | No |
| 4 | M | 35 | 32 | 13 Nov. 2009 | B | 31 | 48 | No | No | No |
| 5 | M | 37 | 32 | 09 Nov. 2009 | B | 34 | 48 | Yes | No | No |
| 6 | F | 70 | 57 | 12 Nov. 2009 | D | 76 | 6 | No | No | No |
| 7 | F | 59 | 34 | 11 Nov. 2009 | B | 51 | 8 | No | Yes | No |
| 8 | F | 67 | 57 | 17 Nov. 2009 | D | 76 | 6 | No | No | No |
| 9 | F | 67 | 56 | 10 Nov. 2009 | D | 73 | 6 | No | No | No |
| 10 | F | 74 | 77 | 20 Nov. 2009 | F | 78 | 48 | No | Yes | No |
| 11 | M | 65 | 31 | 08 Dec. 2009 | B | 25 | 48 | No | No | No |
| 12 | F | 75 | 78 | 20 Nov. 2009 | F | 80 | 4 | No | No | No |
| 13 | F | 59 | 46 | 10 Nov. 2009 | C | 69 | 48 | No | Yes | No |

| Patient | Sex | Age | Biological Age | Visit Date | Type | Age of Arteries | Months of Treatment | Smoker | Additional Medications | Fish Oil Supplement |
|---|---|---|---|---|---|---|---|---|---|---|
| 14 | F | 62 | 57 | 16 Nov. 2009 | D | 74 | 10 | No | Yes | No |
| 15 | M | 74 | 35 | 10 Nov. 2009 | B | 59 | 48 | No | No | No |
| 16 | M | 67 | 56 | 03 Nov. 2009 | D | 64 | 48 | No | No | No |
| 17 | F | 55 | 77 | 12 Nov. 2009 | F | 80 | 48 | No | Yes | No |
| 18 | M | 68 | 68 | 19 Nov. 2009 | E | 78 | 6 | No | Yes | No |
| 19 | M | 54 | 55 | 16 Nov. 2009 | D | 59 | 5 | No | No | No |
| 20 | M | 52 | 33 | 28 Nov. 2009 | B | 46 | 5 | No | No | No |
| 21 | F | 70 | 56 | 18 Nov. 2009 | D | 66 | 48 | No | No | No |
| 22 | F | 64 | 77 | 16 Nov. 2009 | F | 80 | 48 | No | No | No |
| 23 | F | 62 | 35 | 28 Nov. 2009 | B | 57 | 48 | No | Yes | No |
| 24 | F | 72 | 78 | 17 Nov. 2009 | F | 80 | 6 | No | No | No |
| 25 | F | 60 | 67 | 11 Nov. 2009 | E | 76 | 7 | No | No | No |
| 26 | M | 70 | 58 | 10 Nov. 2009 | D | 80 | 6 | No | No | No |
| 27 | F | 60 | 58 | 02 Dec. 2009 | D | 80 | 6 | No | Yes | No |
| 28 | F | 62 | 35 | 08 Dec. 2009 | B | 58 | 48 | No | Yes | No |
| 29 | M | 51 | 56 | 06 Nov. 2009 | D | 62 | 8 | No | Yes | No |
| 30 | F | 35 | 32 | 12 Nov. 2009 | B | 31 | 24 | No | No | No |
| 31 | F | 56 | 56 | 10 Nov. 2009 | D | 67 | 3 | No | Yes | No |
| 32 | F | 67 | 33 | 20 Nov. 2009 | B | 43 | 24 | No | Yes | No |
| 33 | F | 62 | 57 | 05 Nov. 2009 | D | 76 | 24 | No | Yes | No |

One subject showed an age of arteries that was 39 years less than the chronological age. The worst result was a waveform indicative of a patient who had a waveform that was 22 years over the expected physical age. Seventy-three percent (73%) of subjects improved. Overall, the mean age of arteries (flexibility) was 8.82 years less than chronological age. The p value was 15 in 1,000 (p=0.0015), indicating extremely statistically significant results.

This translates to a Number Needed to Treat (NNT) of 1.4 (34 total patients/25 successful outcomes defined as an improvement showing "biological age" of subject cardiovascular system to be less than their physical age). NNT quantifies how many patients need to be treated to see one success. An NNT of less than 50 is considered extremely good.

Twenty-five out of thirty-four patients had biological ages less than their physical age. Included were 5 known diabetic subjects and 1 subject with known significant pre-existing cardiovascular disease. Three (3) of the five (5) diabetic subjects had waveforms expected of a subject having an age inferior to their biological ages. The NNT of medicament success in the diabetic population was 5/-3=1.7.

These results clearly show that the medicament causes reversal of existing heart and cardiovascular diseases in affected subjects, and it is effective in diabetic subjects as well.

Statistical results:

Analysis by Alex Kiss, Ph.D. (statistics) - Jan. 21, 2010
Analysis Variable : agediff

| N | Minimum | Maximum | Mean | Std Dev | Pr > \|t\| |
|---|---|---|---|---|---|
| 34 | -39.00 | 22.00 | -8.82 | 14.84 | 0.0015 |

Short-Term Medicament Results

The short-term effects of the medicament were evaluated in 16 subjects, 9 females and 7 males, ages 46-84, with a median age of 64-years-old. The subjects were administered a daily dose of 2,900 mg of medicament, and the effect of the medicament was evaluated after a period averaging three months. At the end of three months, there was an average improvement by 7.2 years (a lower biological cardiovascular age than the physical age) in the subjects (p=0.99). There were two (2) diabetic subjects; one diabetic subject improved, providing an NNT of 2.0 in the diabetic population.

Analysis by Alex Kiss, Ph.D. (statistics) -Mar. 26, 2010
Analysis Variable : agediff

| N | Mean | Std Dev | Pr > \|t\| |
|---|---|---|---|
| 16 | -7.24 | 10.19 | 0.0099 |

Seven of the 16 subjects improved. The medicament NNT is 16/7=2.3, showing a very high level of effectiveness. These data clearly show that the medicament is highly effective in preventing and treating cardiovascular diseases in affected subjects as well as in diabetic subjects.

Medicament Versus Fish Oil

The effects of the medicament was evaluated in subjects who ceased taking fish oil supplements and were administered a daily dosage of 2,900 mg in place of the fish oil supplements for an average of 3.4 months. The effects of the medicament were measured in five (5) male subjects and one (1) female subject aged 58-71, with a median age of 64.5-years-old, by pulse wave velocity arterial flexibility. The results of the study are shown in the table below:

| Subject | Chronological Age | Biological Age With Fish Oil | Biological Age With Medicament | Length of Treatment (Months) |
|---|---|---|---|---|
| A | 63 | 56 | 34 | 4 |
| B | 69 | 67 | 57 | 1 |
| C | 65 | 54 | 46 | 5.5 |
| D | 61 | 56 | 35 | 1 |
| E | 71 | 35 | 34 | 4 |
| F | 58 | 33 | 33 | 4.5 |

In average, the medicament quickly improved the cardiovascular system's arterial flexibility by over 10 years (younger) in the subjects. Four (4) subjects improved, two (2)

subjects remained the same. No subject was worse with the medicament. Results were statistically significant (p=0.04). Of the five (5) subjects diagnosed with high cholesterol levels who stopped taking fish oil supplements and took the medicament instead, four (4) improved their cardiovascular biological ages. This translates to an NNT of 5/4=1.25 for improvement in cardiovascular system compliance in subjects with high cholesterol manifestations of heart disease. One subject who had both diabetes and high cholesterol diagnosis also showed improvement.

Medicament intervention resulted in an NNT of 6/4=1.5 for the positive result seen in 66% of subjects. These results clearly show that the medicament is superior to fish oil supplements in preventing and reversing cardiovascular disease.

Those of skill in the art will recognize that numerous modifications and changes may be made to the exemplary designs and embodiments described herein and that the invention is not limited to such embodiments.

What is claimed is:

1. A medicament comprising a composition comprising a blend of oils comprising linolcic acid(LA) and α-linolenic acid (ALA) in a LA/ALA ratio that is greater than 1:1 and less than 5:1, wherein the oils in the composition are chemically unprocessed, wherein the composition comprises:
   (i) between about 5% and about 50% of a gamma linolenic acid (GLA)-containing oil; and (ii) a blend of other oils; and wherein the composition does not comprise fish oil, docosahexaenoic acid and eicosapentaenoic acid; and wherein the composition comprises a blend of about 50% organic evening primrose oil, about 33.3% organic flax oil, about 10.7% organic pumpkin oil, and about 5.95% organic virgin coconut oil.

2. The medicament of claim 1, wherein the LA/ALA ratio is within a range from about 2:1 to about 4:1.

3. The medicament of claim 1, wherein the LA/ALA ratio is about 2.6:1.

4. The medicament of claim 1, wherein the composition comprises two or more oils selected from the group consisting of chia, kukui, wheat germ, rice bran, cottonseed, olive, avocado, coconut, palm kernel, beech, brazil nut, pecan, pistachio, hickory, filbert, macadamia, cashew, neem, hemp, flax, pumpkin seed, soybean, walnut, evening primrose, borage, black currant, safflower, sunflower, grape seed, sesame, rape, peanut, almond and corn.

5. The medicament of claim 4, wherein the composition comprises:
   no more than 25% of oleic acid;
   between about 0.1% and about 12% of gamma-linolenic acid; and
   wherein at least 50% of the composition comprises linoleic acid(LA) and α-linolenic acid (ALA) in a LA/ALA ratio that is greater than 1:1 and less than 5:1.

6. The medicament of claim 4, wherein the composition comprises:
   no more than 25% of oleic acid; and
   between about 0.1% and about 12% of gamma-linolenic acid; and
   wherein at least 60% of the composition comprises linoleic acid(LA) and α-linolenic acid (ALA) in a LA/ALA ratio that is greater than 1:1 and less than 5:1.

7. The medicament of claim 4, wherein the composition comprises:
   no more than 25% of oleic acid;
   between about 0.1% and about 12% of gamma-linolenic acid; and
   wherein at least 65% of the composition comprises linoleic acid(LA) and α-linolenic acid (ALA) in a LA/ALA ratio that is greater than 1:1 and less than 5:1.

8. The medicament of claim 1, wherein the composition is in the form of a topical cream for application to the skin.

9. A medicament comprising a composition of oils, said composition of oils being comprised of (i) about 5% to about 50% evening primrose oil, borage oil or black currant oil; and (ii) a blend of other oils, wherein
   (a) the composition comprises linoleic acid(LA) and α-linolenic acid (ALA) in a LA/ALA ratio that is greater than 1:1 and less than 5:1;
   (b) the composition comprises no more than 25% of oleic acid;
   (c) the composition comprises between about 0.1% and about 12% of gamma-linolenic acid;
   (d) the oils in the composition are chemically unprocessed;
   (e) the composition does not comprise fish oil, docosahexaenoic acid and eicosapentaenoic acid; and
   (f) wherein the other oil comprises about 33.3% organic flax oil, about 10.7% organic pumpkin oil, and about 5.95% organic virgin coconut oil.

10. The medicament of claim 9, wherein the composition further includes an antioxidant to reduce oxidation of the medicament.

11. The medicament of claim 9, wherein at least 50% of the composition comprises linoleic acid(LA) and α-linolenic acid (ALA) in a LA/ALA ratio that is greater than 1:1 and less than 5:1.

12. The medicament of claim 9, wherein at least 60% of the composition comprises linoleic acid(LA) and α-linolenic acid (ALA) in a LA/ALA ratio that is greater than 1:1 and less than 5:1.

13. The medicament of claim 9, wherein at least 65% of the composition comprises linoleic acid(LA) and α-linolenic acid (ALA) in a LA/ALA ratio that is greater than 1:1 and less than 5:1.

14. A medicament consisting of:
   about 16.5% evening primrose oil;
   about 34.5% flax oil;
   about 16.5% pumpkin oil;
   about 5.5% coconut oil;
   about 13.5% sunflower oil; and
   about 13.5% safflower oil,
   wherein the oils in the medicament are chemically unprocessed.

15. A medicament consisting of:
   about 16.5% evening primrose oil;
   about 33.0% flax oil;
   about 22.5% pumpkin oil;
   about 5.5% coconut oil; and
   about 22.5% sunflower oil,
   wherein the oils in the medicament are chemically unprocessed.

16. A medicament comprising a composition comprising a blend of oils comprising linoleic acid(LA) and α-linolenic acid (ALA) in a LA/ALA ratio that is greater than 1:1 and less than 5:1, wherein the oils in the composition are chemically unprocessed, wherein the composition comprises no more than 25% of oleic acid; and between about 0.1% and about 12% of gamma-linolenic acid; and wherein the composition comprises a blend of about 50% organic evening primrose oil, about 33.3% organic flax oil, about 10.7% organic pumpkin oil, and about 5.95% organic virgin coconut oil.

17. A method of treating breast cancer in a subject in need thereof, comprising administering to the subject the medicament of claim 1.

18. A method of treating a cardiovascular disease selected from the group consisting of coronary artery disease, peripheral artery disease, and cerebral vascular disease in a subject in need thereof comprising administering to the subject the medicament of claim 1.

* * * * *